(12) United States Patent
Wang et al.

(10) Patent No.: US 8,343,504 B2
(45) Date of Patent: Jan. 1, 2013

(54) METHODS OF ADMINISTERING IGBPMA TO TREAT TYPE 1 HYPERSENSITIVITY

(75) Inventors: Hui Wang, Oxford (GB); Patricia Anne Nuttall, Oxford (GB)

(73) Assignee: Natural Environment Research Council, Wiltshire (GB)

( * ) Notice: Subject to any disclaimer, the term of this patent is extended or adjusted under 35 U.S.C. 154(b) by 488 days.

(21) Appl. No.: 12/092,368

(22) PCT Filed: Oct. 26, 2006

(86) PCT No.: PCT/GB2006/003986
§ 371 (c)(1),
(2), (4) Date: May 1, 2008

(87) PCT Pub. No.: WO2007/051975
PCT Pub. Date: May 10, 2007

(65) Prior Publication Data
US 2008/0280828 A1  Nov. 13, 2008

(30) Foreign Application Priority Data
Nov. 1, 2005 (GB) .................................. 0522298.9

(51) Int. Cl.
*A61K 39/00* (2006.01)
(52) U.S. Cl. .................. 424/191.1; 424/185.1; 424/805; 424/810; 530/350
(58) Field of Classification Search ........................ None
See application file for complete search history.

(56) References Cited

U.S. PATENT DOCUMENTS
2004/0115223 A1   6/2004   Follansbee

FOREIGN PATENT DOCUMENTS
| WO | 95/27056 | 10/1995 |
| WO | WO 9527056 A1 * | 10/1995 |
| WO | 97/44451 | 11/1997 |
| WO | 2004/087188 | 10/2004 |

OTHER PUBLICATIONS

Butterworth, AE., Adv Parasitol. 1984;23:143-235. (abstract only).*
Skolnick et al., Trends in Biotechnology, 18(1):34-39, 2000.*
Whisstock et al., Quarterly Reviews of Biophysics, 2003, 36:307-340.*
Janeway et al, Immunobiology, 3rd edition, 1997, Garland Publishing Inc., pp. 11:12-11:17.*
Wang, H. et al., "Immunoglobulin-G binding proteins in the ixodid ticks, Rhipicephalus appendiculatus, Amblyomma variegatum and Ixodes hexagonus," Parasitology (1995) 111:161-165.
Wang, H. et al., "Immunoglobulin G binding proteins in male Rhipicephalus appendiculatus ticks," Parasite Immunol. (1995) 17:517-524.
International Search Report and Written Opinion for Application No. PCT/GB2006/003986 dated Apr. 24, 2007 (11 pages).
Couillin, I. et al., "Arthropod-derived histamine-binding protein prevents murine allergic asthma," J. Immunol. (2004) 173:3281-3286.
Enriquez, F.J. et al., "Presence of non-fab IgE binding molecules in the intestinal nematode parasite of mice *Heligmosomoides polygyrus*," Int. Arch. Allergy Immunol. (1992) 99:123-126.
Koshino, S.S. et al., "*Boophilus microplus*: the pattern of bovine immunoglobulin isotype responses to high and low tick infestations," Exp. Parasitology (2005) 110:12-21.
Szabo, M.P.J. et al., "Antibody and blood leukocyte response in *Rhipicephalus sanguineus* (Latreille, 1806) tick-infested dogs and guinea pigs," Vet. Parasitology (2003) 115:49-59.
Vincendeau, P. et al., "Trypanosoma musculi co-express several receptors binding rodent IgM, IgE, and IgG subclasses," J. Immunol. (1989) 142(5):1702-1709.
Wang, H. et al., "Male ticks help their mates to feed," Nature (1998) 391:753-754.
Wang, H. et al., "Excretion of host immunoglobulin in tick saliva and detection of IgG-binding proteins in tick haemolymph and salivary glands," Parasitology (1994) 109:525-530.
Wang, H. et al., "Immunoglobulin-binding proteins in ticks: new target for vaccine development against a blood-feeding parasite," Cell Mol. Life Sci. (1999) 56(3-4):286-295 (Abstract only).
Japanese Patent Office Action for Application No. 2008-538390 dated Feb. 3, 2012 (7 pages—English Translation).
Gwakisa, P. et al., Veterinary parasitology, 2001, vol. 99, No. 1, p. 53-61.
The Current Medical Dictionary, 2nd Ed, Ishiyaku Pub, Inc., 2001, p. 982, The term "Generalized (Systemic) anaphylaxis" (excerpt).
Chinese Patent Office Examination Report for Application No. 200680050239.3 dated May 10, 2012 (6 pages—English translation).
Pharmacological Basis for Anti-JgE Treatment, Zhongqiu Liu et al., Foreign Medical Sciences (Section of Respiratory System), 2001,vol. 21, No. 4, pp. 209-212.
Non-immunological Factors of Allergic Rhinitis, Zhiyan Gu, Tianjin Medical Journal, 1991, No. 7, pp. 445-448.
Clinical Observation of JgG Change in Asthma Outbreak, Degui Kong et al., Chinese Journal of Primary Medicine and Pharmacy, vol. 7, No. 5, p. 353, 2000.

(Continued)

*Primary Examiner* — Michael Szperka
(74) *Attorney, Agent, or Firm* — Michael Best & Friedrich LLP

(57) ABSTRACT

The present invention relates generally to methods and materials for treating conditions associated with IgE activation in humans and animals, and to agents capable of modulating the activation. The agents of the invention comprise or are related to IGBPMA polypeptides from ticks.

2 Claims, 11 Drawing Sheets

OTHER PUBLICATIONS

Figure 3:
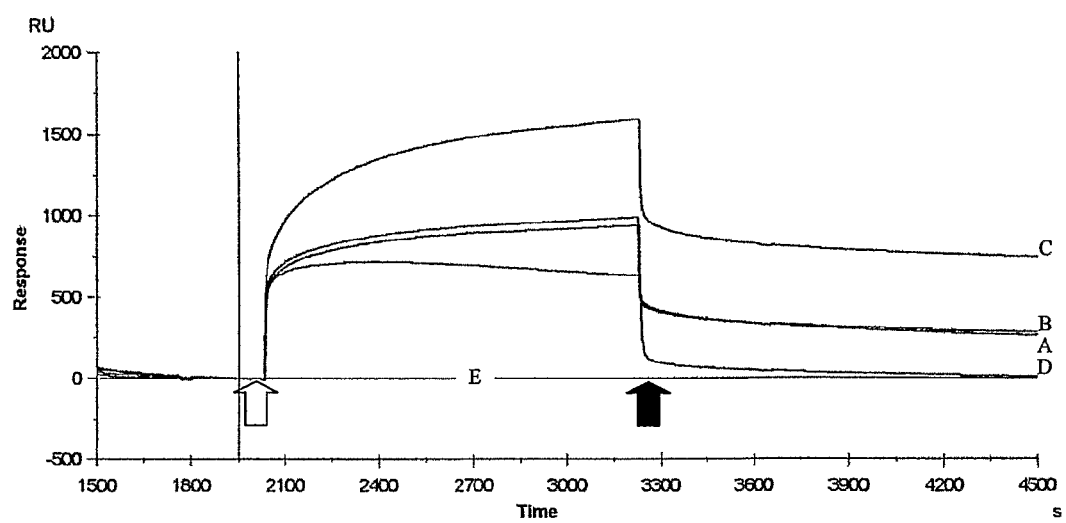

Metz et al., Omalizumab in chronic urticaria, Curr Opin Allergy Clin Immunol 2012, 12:406-411.

ME Ramirez Del Pozo et al., Omalizumab (an Anti-IgE Antibody) in the Treatment of Severe Atopic Eczema, J Investig Allergol Clin Immunol 2011; vol. 21(5): 410-421.

Vichyanond et al., Omalizumab in allergic diseases, a recent review, Asian Pac J Allergy Immunol 2011; 29:209-19.

Stone et al., Immunomodulatory Therapy of Eosinophil-Associated Gastrointestinal Diseases, Clin Exp Allergy. Dec. 2008; 38(12): 1858-1865.

Velling et al., Improvement of Quality of Life in Patients With Concomitant Aliergic Asthma and Atopic Dermatitis: One Year Follow-Up of Omalizumab Therapy, Eur J Med Res (Sep. 12, 2011) 15:407-410.

Busse et al., Omalizumab, anti-IgE recombinant humanized monoclonal antibody, for the treatment of severe allergic asthma, J Allergy Clin Jmmunol, Aug. 2001, vol. 108, No. 2 (7 pages).

* cited by examiner

*IGBP-MA:*

```
       ATGATGCTAGAAGCTTTTGGCGTGAAATTCACCAAAACCGGAACGGGCACCTCCCAGGCG
  1    ------------+----------+----------+----------+----------+----------+   60
       M  M  L  E  A  F  G  V  K  F  T  K  T  G  T  G  T  S  Q  A

GCCTACAATGGTAAAAAATACGAAGTGTACACAGGGCGCGGGGTAACCATCACCGTCGAC
 61    ------------+----------+----------+----------+----------+----------+  120
       A  Y  N  G  K  K  Y  E  V  Y  T  G  R  G  V  T  I  T  V  D

AATACGCAATATGAAATTCCGGCAGACCTCGAGAAGATATTCCAGAAACCAAAGGGCTTC
121    ------------+----------+----------+----------+----------+----------+  180
       N  T  Q  Y  E  I  P  A  D  L  E  K  I  F  Q  K  P  K  G  F

AGCGTGGGCTCACTGCTCGTAGCTTTGCAGGAAAAGGGCATCCCGGTGAATGTGGACGAA
181    ------------+----------+----------+----------+----------+----------+  240
       S  V  G  S  L  L  V  A  L  Q  E  K  G  I  P  V  N  V  D  E

AAAACGGGTGTCATCCTCGGCATCACCATCGACAAAGTGCGAGTTCCGTTCCCGGTTTCC
241    ------------+----------+----------+----------+----------+----------+  300
       K  T  G  V  I  L  G  I  T  I  D  K  V  R  V  P  F  P  V  S

ATCGACCTGCGCTTTAAGCTGGACAACCAAATTTACCTAATACCGCGCGACCTCGCCAAG
301    ------------+----------+----------+----------+----------+----------+  360
       I  D  L  R  F  K  L  D  N  Q  I  Y  L  I  P  R  D  L  A  K

CTGATCACCGTGCTCGAAAAGAAAGGCATGCCCAGCAAGATCCTGTTCATTTTGTACACC
361    ------------+----------+----------+----------+----------+----------+  420
       L  I  T  V  L  E  K  K  G  M  P  S  K  I  L  F  I  L  Y  T

CGCTACGGAGTCGTTCCTGTGCGAGATTCCAACGGTATCGTCGTCGCCATCTCCTTCAAC
421    ------------+----------+----------+----------+----------+----------+  480
       R  Y  G  V  V  P  V  R  D  S  N  G  I  V  V  A  I  S  F  N

GGCAAGCAGTTCAAGGTCAAGCCGGAGCCACTCACTGCCGTGGTGATTCTGGGTCAGAAG
481    ------------+----------+----------+----------+----------+----------+  540
       G  K  Q  F  K  V  K  P  E  P  L  T  A  V  V  I  L  G  Q  K

TTCATACTGCCCAGGGACACGAGAAAAATGGTCGAGTTCGTGCACTCCAAGCAGAGTCAT
541    ------------+----------+----------+----------+----------+----------+  600
       F  I  L  P  R  D  T  R  K  M  V  E  F  V  H  S  K  Q  S  H

CCAGAGATCGGTTTCATCTTCTTGAAGGCTCTGAAGAGTGCTGGCTTCATGCTTATCAAC
601    ------------+----------+----------+----------+----------+----------+  660
       P  E  I  G  F  I  F  L  K  A  L  K  S  A  G  F  M  L  I  N

GACGATGACGGTGCGATGCGCTCGATCCAGAAGGGGGCGCAGATAATCAAGCTCGGTTTT
661    ------------+----------+----------+----------+----------+----------+  720
       D  D  D  G  A  M  R  S  I  Q  K  G  A  Q  I  I  K  L  G  F

GAAATAAGAATACAGGTGATTTATGGCAAAACCACTTACCACGTGCCCAAGGATCTGATG
721    ------------+----------+----------+----------+----------+----------+  780
       E  I  R  I  Q  V  I  Y  G  K  T  T  Y  H  V  P  K  D  L  M

CGACTTGTGAAAGACGTCCGCAGCCTTGGGCCCCAGGAAATCCAAAGTGTCATGAAGCAA
781    ------------+----------+----------+----------+----------+----------+  840
       R  L  V  K  D  V  R  S  L  G  P  Q  E  I  Q  S  V  M  K  Q

CTCAAAGCTTTCGACGTGCAAGTAAAGAAGGAGGGCAGCAAGCTTACCATACTCTTCAAC
841    ------------+----------+----------+----------+----------+----------+  900
       L  K  A  F  D  V  Q  V  K  K  E  G  S  K  L  T  I  L  F  N

AGCGTCCGATACGAGGTAGACCTCAAGTCCGGTAACGTCAAGGGATAGCAGTTCCAAGAA
901    ------------+----------+----------+----------+----------+----------+  960
       S  V  R  Y  E  V  D  L  K  S  G  N  V  K  G

ACGAGATGACACGCTTCAGCCGGTGGCCACCGTGGCGCGCCCCACGAGAACGCACTACGC
961    ------------+----------+----------+----------+----------+----------+ 1020

GTTACCGAGGGGCATTTTGGACCATGTTGAATAAACAAGTCGCACATTAAAAAAAAAA
1021   ------------+----------+----------+----------+----------+---------   1078
```

Figure 1

A. Salivation of males and females by DA stimulation
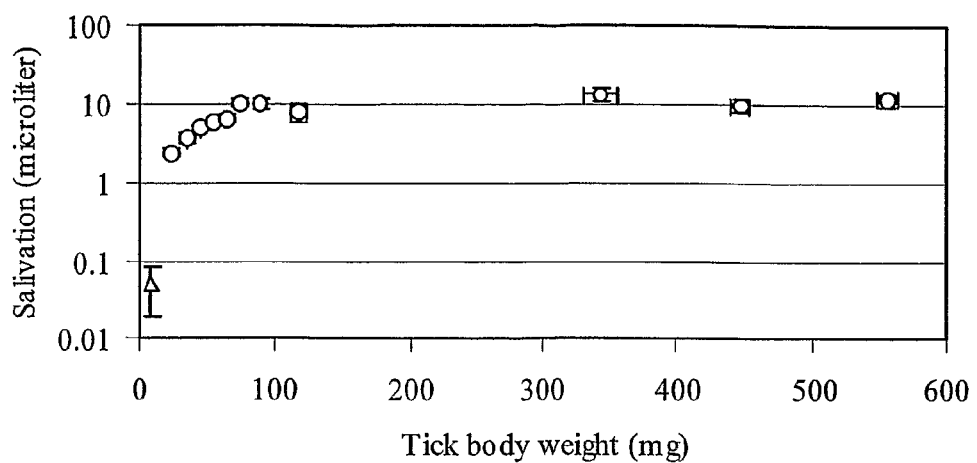
B. Protein concentration in tick saliva
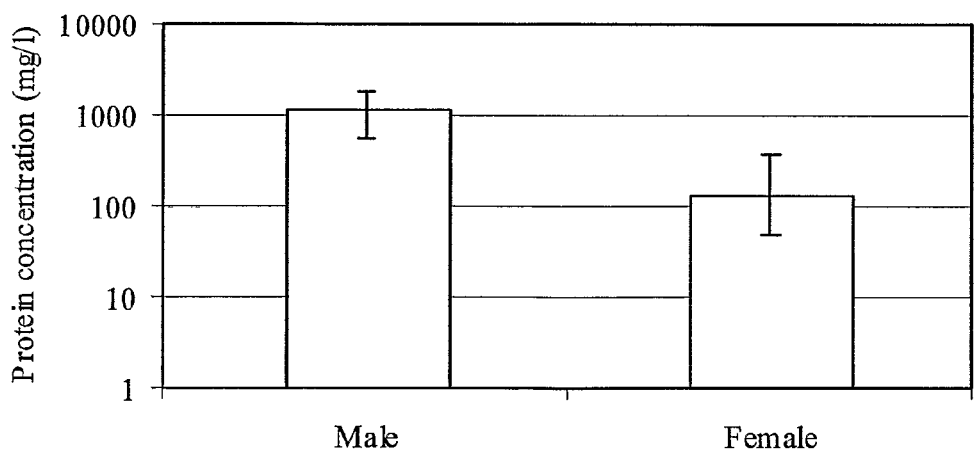
Figure 2

SEQUENCE LISTING

<160> NUMBER OF SEQ ID NOS: 4

<210> SEQ ID NO 1
<211> LENGTH: 1078
<212> TYPE: DNA
<213> ORGANISM: Rhipicephalus appendiculatus

<400> SEQUENCE: 1

```
atgatgctag aagcttttgg cgtgaaattc accaaaaccg gaacgggcac ctcccaggcg      60
gcctacaatg gtaaaaaata cgaagtgtac acagggcgcg gggtaaccat caccgtcgac     120
```

-continued

```
aatacgcaat atgaaattcc ggcagacctc gagaagatat tccagaaacc aaagggcttc    180
agcgtgggct cactgctcgt agctttgcag gaaaagggca tcccggtgaa tgtggacgaa    240
aaaacgggtg tcatcctcgg catcaccatc gacaaagtgc gagttccgtt cccggtttcc    300
atcgacctgc gctttaagct ggacaaccaa atttacctaa taccgcgcga cctcgccaag    360
ctgatcaccg tgctcgaaaa gaaaggcatg cccagcaaga tcctgttcat tttgtacacc    420
cgctacggag tcgttcctgt gcgagattcc aacggtatcg tcgtcgccat ctccttcaac    480
ggcaagcagt tcaaggtcaa gccggagcca ctcactgccg tggtgattct gggtcagaag    540
ttcatactgc ccagggacac gagaaaaatg gtcgagttcg tgcactccaa gcagagtcat    600
ccagagatcg gtttcatctt cttgaaggct ctgaagagtg ctggcttcat gcttatcaac    660
gacgatgacg gtgcgatgcg ctcgatccag aaggggcgc agataatcaa gctcggtttt    720
gaaataagaa tacaggtgat ttatggcaaa accacttacc acgtgcccaa ggatctgatg    780
cgacttgtga agacgtccg cagccttggg ccccaggaaa tccaaagtgt catgaagcaa    840
ctcaaagctt tcgacgtgca agtaaagaag gagggcagca agcttaccat actcttcaac    900
agcgtccgat acgaggtaga cctcaagtcc ggtaacgtca agggatagca gttccaagaa    960
acgagatgac acgcttcagc cggtggccac cgtggcgcgc cccacgagaa cgcactacgc   1020
gttaccgagg ggcattttgg accatgttga ataaacaagt cgcacattaa aaaaaaa     1078
```

<210> SEQ ID NO 2
<211> LENGTH: 315
<212> TYPE: PRT
<213> ORGANISM: Rhipicephalus appendiculatus

<400> SEQUENCE: 2

```
Met Met Leu Glu Ala Phe Gly Val Lys Phe Thr Lys Thr Gly Thr Gly
1               5                   10                  15

Thr Ser Gln Ala Ala Tyr Asn Gly Lys Lys Tyr Glu Val Tyr Thr Gly
            20                  25                  30

Arg Gly Val Thr Ile Thr Val Asp Asn Thr Gln Tyr Glu Ile Pro Ala
        35                  40                  45

Asp Leu Glu Lys Ile Phe Gln Lys Pro Lys Gly Phe Ser Val Gly Ser
    50                  55                  60

Leu Leu Val Ala Leu Gln Glu Lys Gly Ile Pro Val Asn Val Asp Glu
65                  70                  75                  80

Lys Thr Gly Val Ile Leu Gly Ile Thr Ile Asp Lys Val Arg Val Pro
                85                  90                  95

Phe Pro Val Ser Ile Asp Leu Arg Phe Lys Leu Asp Asn Gln Ile Tyr
            100                 105                 110

Leu Ile Pro Arg Asp Leu Ala Lys Leu Ile Thr Val Leu Glu Lys Lys
        115                 120                 125

Gly Met Pro Ser Lys Ile Leu Phe Ile Leu Tyr Thr Arg Tyr Gly Val
    130                 135                 140

Val Pro Val Arg Asp Ser Asn Gly Ile Val Val Ala Ile Ser Phe Asn
145                 150                 155                 160

Gly Lys Gln Phe Lys Val Lys Pro Glu Pro Leu Thr Ala Val Val Ile
                165                 170                 175

Leu Gly Gln Lys Phe Ile Leu Pro Arg Asp Thr Arg Lys Met Val Glu
            180                 185                 190

Phe Val His Ser Lys Gln Ser His Pro Glu Ile Gly Phe Ile Phe Leu
        195                 200                 205

Lys Ala Leu Lys Ser Ala Gly Phe Met Leu Ile Asn Asp Asp Asp Gly
```

```
                    210             215             220
Ala Met Arg Ser Ile Gln Lys Gly Ala Gln Ile Ile Lys Leu Gly Phe
225                 230                 235                 240

Glu Ile Arg Ile Gln Val Ile Tyr Gly Lys Thr Thr Tyr His Val Pro
                245                 250                 255

Lys Asp Leu Met Arg Leu Val Lys Asp Val Arg Ser Leu Gly Pro Gln
                260                 265                 270

Glu Ile Gln Ser Val Met Lys Gln Leu Lys Ala Phe Asp Val Gln Val
            275                 280                 285

Lys Lys Glu Gly Ser Lys Leu Thr Ile Leu Phe Asn Ser Val Arg Tyr
    290                 295                 300

Glu Val Asp Leu Lys Ser Gly Asn Val Lys Gly
305                 310                 315

<210> SEQ ID NO 3
<211> LENGTH: 40
<212> TYPE: DNA
<213> ORGANISM: Artificial sequence
<220> FEATURE:
<223> OTHER INFORMATION: Synthetic sequence: Primer

<400> SEQUENCE: 3
agtgcggccg ctcccttgac gttaccggac ttgaggtcta                    40

<210> SEQ ID NO 4
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 4
agttctagac atatgaaata cgaagtgtac acagggcgcg gggt              44
```

METHODS OF ADMINISTERING IGBPMA TO TREAT TYPE 1 HYPERSENSITIVITY

CROSS-REFERENCE TO RELATED APPLICATIONS

This patent application is a national stage filing under 35 U.S.C. 371 of International Application No. PCT/GB2006/003986, filed on Oct. 26, 2006, which claims foreign priority benefits to United Kingdom Patent Application No. 0522298.9, filed on Nov. 1, 2005.

FIELD OF THE INVENTION

The present invention relates generally to methods and material for treating conditions associated with IgE activation in humans and animals, and to agents capable of modulating the activation.

BACKGROUND TO THE INVENTION

IgE is a class of antibody involved in allergic reactions. These reactions occur when an individual who has produced IgE antibody in response to an innocuous antigen (allergen sensitisation) subsequently encounters the same allergen. The allergen triggers the activation of IgE-binding mast cells in the exposed tissue leading to a series of responses that are characteristic of allergy.

IgE is the immunoglobulin associated with Type I hypersensitivity reactions, which include asthma, allergic rhinitis ('hay fever'), allergic conjunctivitis, urticaria and other allergies. Over-expression of this antibody is responsible for a substantial amount of human disease ranging from mild hay fever to life-threatening conditions such as severe asthma, peanut allergy and anaphylactic reactions to drugs such as penicillin. Activation of IgE triggers the response of cells such as mast cells in the skin, eyes, nose and bronchial tree.

Current approaches aimed at counteracting the unwanted effects of IgE activation include anti-IgE vaccines and anti-IgE monoclonal antibodies. The former are largely experimental. The anti-IgE monoclonal antibody approach has been more successful, although at present there is only a single example on the market (omalizumab, brand name Xolair®).

Thus it can be seen that a novel source of IgE modulators would provide a contribution to the art.

DISCLOSURE OF THE INVENTION

The present inventors analysed tick (*Rhipicephalus appendiculatus*) salivary gland extracts and saliva for immunoglobulin binding activities and surprisingly discovered that tick salivary glands and saliva contain IgE-binding activity.

It was known that host IgG, IgM, and IgE are involved in some way in host anti-tick responses (Allen, Khalil & Graham, 1979; Beaudouin et al., 1997; Christe, Rutti & Brossard, 1999; Fivaz, 1990; Matsuda et al., 1990; Mitchell, Brown & Askenase, 1982; Ushio et al., 1993; Brown & Askenase, 1985; Worms, Askenase & Brown, 1988). It was believed that the host immunoglobulins are ingested by ticks with the blood meal, some of which pass to the haemolymph where they retain their biological activity (Ackerman et al., 1981; Chinzei & Minoura, 1987; Tracey Patte, Kemp & Johnston, 1987; Wang & Nuttall, 1994). Thus, if ticks feed on a host previously exposed to the species, antibodies specific for tick antigens may enter the ticks' haemocoel.

To counter this potential threat, it is believed that *R. appendiculatus* can excrete these immunoglobulins back into the host via their salivary secretions (Wang & Nuttall, 1994). Additionally, proteins that bind IgG have been found in ticks (Wang & Nuttall, 1995 a and b; Wang & Nuttall, 1999; WO95/27056). These IgG binding proteins include IGBPMA, IGBPMB and IGBPMC.

Unexpectedly, the present inventors have discovered that the IgE binding activity disclosed herein is provided by protein IGBPMA, with amino acid sequence shown in SEQ ID NO: 2 that is encoded by the nucleotide sequence shown in SEQ ID NO: 1.

This is surprising since an anti-IgE response to tick infestation has not been discussed in the literature. Indeed the role of IgE in the host response is rather unclear. For example, dog serum IgE levels increased significantly after *Rhipicephalus sanguineus* infestation, but no change in the amount of tick anti-salivary gland IgE was detected. The authors explained this as non-specific inducement of an immune environment favourable for IgE production against other unrelated antigens (Szabo, Aoki et al. 2003). IgE production was also induced by *Amblyomma cajennense* infestation in donkeys (Szabo, Castagnolli et al. 2004). After repeated infestation by *Boophilus microplus*, cattle of tick-susceptible breeds decreased IgG antibody levels but increased IgE antibody levels, to the tick salivary gland antigens, indicating tick saliva components suppressed IgG response but induced IgE response in tick-susceptible cattle (Kashino, Resende et al. 2005). The authors concluded that IgE antibodies were not protective. This also conforms with the observation that *Ixodes ricinus* infestations polarise a Th2 response with a gradual increase in total IgE in mice (Christe, Rutti et al. 1999; Christe, Rutti et al. 2000).

The combination of the evidence of IgG-binding proteins, the presence of histamine-binding proteins in tick salivary glands, and the absence of reports of IgE-binding proteins, means that the generally held view in the literature prior to the present disclosure was that host IgE responses to tick infestations were not protective and that IgE antibodies were unlikely to have a role in controlling tick infestations.

The fact that ticks do indeed produce IgE-binding molecules is therefore quite unexpected. In the light of the present disclosure it appears that injection by ticks of IgE binding activity (perhaps in the form of soluble IgE receptors) into the feeding site may suppress local IgE-mediated activation of the effector cells such as mast cells and basophils which occurs through cross linking of receptors on the surface of those cells (Brossard & Wikel, 1997; Brown, Worms & Askenase, 1983; Matsuda et al., 1990; Szabo & Bechara, 1999; Ushio et al., 1993; Kinet, 1999). This may facilitate tick blood feeding.

There have been only two reports in the literature that any parasite produces an IgE-binding activity. Receptor activities to the Fc portion of rodent Ig (IgG, IgM, and IgE) were detected in the murine parasite *Trypanosoma musculi* (Vincendeau & Daeron, 1989), and non-Fab binding activity to host IgE was reported for the murine nematode parasite, *Heligmosomoides polygyrus* (Enriquez, Boggavarapu & Bradley Dunlop, 1992). However, no IgE binding molecules were isolated from these organisms. An alternative mechanism has been detected in *Leishmania chagasi* in which the protozoan inhibits the expression of the IgE low-affinity receptor (CD23) of B-lymphocytes and macrophages (Noben, Wilson & Lynch, 1994).

Thus the inventors have provided a novel source of IgE-binding molecules. They have further investigated the IgE-binding activity of IGBPMA and have shown it has effect in a mouse anti-asthma model, suggesting the protein may form the basis for a novel treatment of conditions associated with IgE activation, such as allergic conditions. Based on the results of other tick-derived proteins immunogenicity is also likely to be low (e.g. EV131, from Evolutec Group plc. UK—see WO9744451).

In various aspects the invention relates to generally, inter alia, to new medical use of IGBPMA, and polypeptides and other agents that are related to IGBPMA, to bind IgE in mammals, thereby to modulate its action and to control its pathological effects, for example in the treatment of conditions associated with IgE activation.

These and other aspects of the present invention will now be discussed in more detail.

Medical Uses

Thus in one aspect the invention provides use of a polypeptide in the manufacture of a medicament for the treatment of a condition associated with IgE activation, wherein polypeptide comprises:
(i) the amino acid sequence shown in FIG. 1 (SEQ ID NO: 2),
(ii) a variant of the amino acid sequence shown in FIG. 1 (SEQ ID NO: 2) sharing at least 50, 60, 70, 80, 90, 95, or 99% identity with at least 200, 250, 275, 300, 310 contiguous amino acids therein, or
(iii) a fragment of the amino acid sequence shown in FIG. 1 (SEQ ID NO: 2) having at least 150, 200, 250, 275, 300, 210 contiguous amino acids shown therein,
wherein in each case the polypeptide is capable of binding an IgE molecule.

Preferably the variant shares the specified level of identity with the full length amino acid sequence shown in FIG. 1 (SEQ ID NO: 2).

The polypeptides of the present invention are capable of binding IgE, and in particular binding to one or more binding sites on the constant region of IgE (for example to suppress IgE-mediated activation of the effector cells as discussed above) i.e. the binding is not merely that of an antigen to the variable region of the IgE.

Preferably the binding to IgE is equal to or stronger than binding to IgG.

Binding activity may be confirmed using any method known to those skilled in the art, for example any of the methods below (including SPL, for example using a BIAcore instrument, or using IgE affinity chromatography). IgE molecules used to screen for binding affinity may be obtained, for example, from human, rat, mouse, rabbit, or any other animal which produces IgE. Fragments of IgE molecules used to screen for activity may comprise all or part of the Fc and/or the F(ab')2 regions (but will not merely consist of IgE variable regions).

As used herein, the term "condition associated with IgE activation" includes allergic conditions. Such allergic conditions may involve the production of IgE in response to certain antigens. Such allergic conditions may be Type I hypersensitivity reactions, for example. Type I hypersensitivity reactions include asthma, eczema, allergic rhinitis, rhinorrhea, conjunctivitis, gastroenteritis, urticaria, or anaphylactic reactions.

In another aspect the invention provides use of a nucleic acid molecule, which encodes a polypeptide as described above, in the manufacture of a medicament for the treatment of a condition associated with IgE activation, wherein the nucleic acid comprises:
(i) the nucleotide sequence shown in FIG. 1 (SEQ ID NO: 1),
(ii) a variant of the coding nucleotide sequence shown in FIG. 1 (SEQ ID NO: 1) sharing at least 50, 60, 70, 80, 90, 95, or 99% identity with at least 600, 750, 875, 900, 930 contiguous nucleotides therein,
(iii) a fragment of the nucleotide sequence shown in FIG. 1 (SEQ ID NO: 1) having at least 450, 600, 750, 825, 900, 930 contiguous nucleotides shown therein.

Preferably the variant shares the specified level of identity with the full length nucleotide sequence shown in FIG. 1 (SEQ ID NO: 1).

Embodiments of the invention relating to variants will now be discussed in more detail.

Variants

Variant IGBPMA molecules (polypeptides and nucleotides) of the present invention may be:

(i) novel, naturally occurring, homologous IGBP molecules, for example obtainable from ectoparasites e.g. other species of ticks or arthropod parasites, for example as discussed herein. Also included are natural biological variants (e.g. allelic variants or geographical variations) of *R. appendiculatus* IGBPMA. Preferred sources of IGBP molecules are ectoparasites and especially, but not exclusively, the blood-feeding insect and acarine parasites, e.g. biting flies, cattle ticks and mites. As representative of such arthropod parasites may be mentioned for example, ticks of the species *Boophilus, Amblyomma, Argas, Rhipicephalus, Hyalomma, Ornithodorus, Dermacentor, Ixodes*; flies, particularly the myiasis, sucking and biting flies, such as *Oestrus ovis, Gasterophilus* spp, *Chrysomyia* spp, *Calliphora* spp, *Hypoderma* spp, *Dermatobia* spp, *Cochliomyla* spp, *Stomoxys calcitrans, Hydrotaea irritans, Simulium* spp, *Lyperosia irritans. Haematobia* spp, *Tabanus* spp, *Phlebotomus* spp and *Glossina* spp, lice e.g. *Haematopinus eurysternus, Linognathus vituli, Solenopotes capillatus, Linoanathus ovillus*, and *Menacanthus* spp; mites such as *Notoedres* spp, *Demodex* spp, *Sarcoptes* spp, *Chorioptes* spp, *Psoreraates* spp, *Dermanyssus* spp, *Ornithonyssus* spp, *Otodectes* spp and *Notoedres* spp; fleas e.g. *Ctenocephalides canis* and *C. felis*; keds e.g. *Melophagus ovinus* and bugs such as *Cimex* spp.

(ii) artificial IGBPMA molecule derivatives, which can be prepared by the skilled person in the light of the present disclosure. Such derivatives may be prepared, for instance, by site directed or random mutagenesis, or by direct synthesis. Preferably a variant nucleic acid (for example) is generated either directly or indirectly (e.g. via one or more amplification or replication steps) from an original nucleic acid having all or part of the sequence shown herein as SEQ ID NO: 1.

Particularly included are truncated variants which include only a distinctive part or fragment (however produced) corresponding to a portion of the sequences herein—for example functional parts of the polypeptide capable of binding IgE.

Also included are molecules which have been extended at their termini with non-naturally contiguous sequences i.e. polypeptides of the invention may also comprise additional amino acids, additional domains, or may be conjugated to additional domains or other molecules. Additional amino acids, domains, or molecules conjugated to the polypeptide may provide an additional function, for example in assisting purification of the polypeptide. Examples of additional domains that may assist in purification of the polypeptide are 6-histidine tag, and glutathione S-transferase tag. Polypeptides may be fusion proteins, fused to a peptide or other protein, such as a label, which may be, for instance, bioactive, radioactive, enzymatic or fluorescent.

The term 'variant' nucleic acid as used herein encompasses all of these possibilities. When used in the context of polypeptides or proteins it indicates the encoded expression product of the variant nucleic acid, and vice versa.

Some of the aspects of the present invention relating to variants will now be discussed in more detail.

The percent identity of two amino acid or two nucleic acid sequences can be determined by visual inspection and mathematical calculation, or more preferably, the comparison is done by comparing sequence information using a computer program. An exemplary, preferred computer program is the Genetics Computer Group (GCG; Madison, Wis.) Wisconsin package version 10.0 program, 'GAP' (Devereux et al., 1984, Nucl. Acids Res. 12: 387). The preferred default parameters for the 'GAP' program includes: (1) The GCG implementation of a unary comparison matrix (containing a value of 1 for identities and 0 for non-identities) for nucleotides, and the weighted amino acid comparison matrix of Gribskov and Burgess, Nucl. Acids Res. 14:6745, 1986, as described by Schwartz and Dayhoff, eds., Atlas of Polypeptide Sequence and Structure, National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps.

Production of Derivatives

Derivatives may be produced by modifying any of the sequences disclosed herein.

The polypeptides of the invention may be a truncated fragment e.g. N-terminal 26 amino acid truncated. Such fragments may be provided in isolated form i.e. not part of or fused to other amino acids or polypeptides, or they may be comprised within a larger polypeptide of which they form a part or region. When comprised within a larger polypeptide, the fragment of the invention most preferably forms a single continuous region with one or two non-naturally contiguous sequences fused to it. Additionally, several fragments may be comprised within a single larger polypeptide.

Changes to nucleic acid sequences may be desirable for a number of reasons. For instance they may introduce or remove restriction endonuclease sites or alter codon usage. Alternatively changes to a sequence may produce a derivative by way of one or more of addition, insertion, deletion or substitution of one or more nucleotides in the nucleic acid, leading to the addition, insertion, deletion or substitution of one or more amino acids in the encoded polypeptide.

Such changes may modify sites which are required for post translation modification such as cleavage sites in the encoded polypeptide; motifs in the encoded polypeptide for glycosylation, lipoylation etc. Leader or other targeting sequences (e.g. membrane or golgi locating sequences) may be added to the expressed protein to determine its location following expression.

Other desirable mutation may be random or site directed mutagenesis in order to alter the activity (e.g. specificity) or stability of the encoded polypeptide. Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation. Also included are variants having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may confer advantageous properties on the polypeptide. Indeed, changes such as those described above may confer slightly advantageous properties on the peptide e.g. altered stability or specificity.

The variants and/or homologues of the invention may also be created by chemical modification of IGBPMA. Methods for chemical modification of polypeptides are well known in the art.

Polypeptides of the invention may be obtained by expression of a nucleic acid that encodes the polypeptide using a suitable vector and host organism. Examples of suitable vectors and hosts are well known in the art (see e.g. Sambrook, J. et al. (1989) in: Molecular Cloning: A Laboratory Manual (2nd ed.), Cold Spring Harbor Laboratory Press, New York).

Polypeptides, and particularly fragments, of the invention may also be created using chemical synthesis by any suitable method, such as by exclusively solid-phase techniques, by partial solid-phase techniques, by fragment condensation or by classical solution couplings. In conventional solution phase peptide synthesis, the peptide chain can be prepared by a series of coupling reactions in which the constituent amino acids are added to the growing peptide chain in the desired sequence. Many such methods are now commonplace to those skilled in the art.

The variants and/or homologues of the invention may also be created by modification, using molecular biological techniques, of the nucleic acid that encodes IGBPMA, or a nucleic acid that encodes a further variant or homologue of the invention. Molecular biological techniques are well known in the art.

Thus the invention provides a method of producing an IgE modulating polypeptide which method comprises the steps of (i) providing a polypeptide which is IGBPMA or a variant thereof, or nucleic acid encoding therefor,
(ii) modifying the sequence of the polypeptide, or nucleic acid encoding therefor, and
(iii) assaying the IgE binding properties of the modified polypeptide (where nucleic acid is modified, this is the expression product of the modified nucleic acid).

For brevity hereinafter, IGBPMA and variant polypeptides may be referred to as "IGBPMA polypeptides".

Identification of Homologues

Antibodies to IGBPMA polypeptides may be used to screen for IgE binding compounds having structural similarity to those specifically exemplified herein. Suitable methods are well known to those skilled in the art.

Once a binding activity is identified, methods of purifying polypeptides from heterogenous mixtures are well known in the art (e.g. selective precipitation, proteolysis, ultrafiltration with known molecular weight cut-off filters, ion-exchange chromatography, gel filtration, etc.) Typical protocols are set out "Protein Purification"—principles and practice" Pub. Springer-Verlag, New York Inc (1982), and by Harris & Angal (1989) "Protein purification methods—a practical approach" Pub. O.U.P. UK, or references therein. Further methods which are known to be suitable for protein purification are disclosed in "Methods in Enzymology Vol 182—Guide to Protein Purification" Ed. M P Deutscher, Pub. Academic Press Inc.

The IGPBMA sequence (AF001868) may be used in a data-base (e.g. of ESTs, or STSs) search to find homologous sequences, such as those which may become available in due course, and expression products of which can be tested for activity as described herein.

Alternatively homologues may be provided by standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells. Probing may optionally be done by means of so-called 'nucleic acid chips' (see Marshall & Hodgson (1998) Nature Biotechnology 16: 27-31, for a review).

Libraries of nucleic acid molecules may be created which may be screened for nucleic acids that encode a polypeptide capable of binding an IgE molecule. Such libraries may be created using the nucleic acid molecule that encodes IGBPMA. The IGBPMA nucleic acid molecule sequence may be mutated, for example using random PCR mutagenesis, or gene shuffling techniques. The resulting mutated nucleic acid molecules may be ligated into a vector. Libraries of polypeptides may be created, by expressing the nucleic acid molecules in a suitable host.

Nucleotide variants of the present invention will preferably be 'hybridising sequences', which are those binding under non-stringent conditions (6×SSC/50% formamide at room temperature) and washed under conditions of low stringency (2×SSC, room temperature, or 2×SSC, 42° C.) or more preferably conditions of higher stringency, e.g. 2×SSC, 65° C. (where SSC=0.15M NaCl, 0.015M sodium citrate, pH 7.2).

Alternatively, a nucleic acid amplification reaction, particularly the polymerase chain reaction (PCR) may be used (see "PCR protocols; A Guide to Methods and Applications", Eds. Innis et al, Academic Press, New York, (1990)). Obtained sequences may be compared with the IGBPMA reference sequence in the GenBank nucleotide sequence (AF001868) by using BESTFIT in the GCG package.

In the Examples herein a variant sequence (SEQ ID NO: 1) comprising a silent mutation (T-C) at nt-648 of the IGBPMA reference sequence (GenBank, AF001868) is disclosed.

As discussed hereinafter, the invention also provides IGBPMA mimetics, or other agents identified based on the IGBPA-IgE interaction.

Unless context demands otherwise, in the disclosure hereinafter, any of the aforementioned polypeptides, polynucleotides, variants of either, mimetics or other agents of the invention may be referred to as a 'therapeutic of the invention', and the disclosure in respect of such therapeutics applies to each of these things individually. In all cases preferred therapeutics of the invention are the polypeptides or polynucleotides (including variants or fragments of either) of the preceding aspects, and in particular to the IGBPMA polypeptides (including variants or fragments thereof).

All such therapeutics are disclosed for use in the treatment of conditions associated with IgE activation. Likewise methods of their use are disclosed (in addition to their use in preparing medicaments for such treatments).

All such therapeutics may also be tested for safety and/or toxicity in a human or animal subject for efficacy in treating conditions associated with IgE activation and may be formulated with one or more carriers, diluents or agents for the treatment of conditions associated with IgE activation as described below.

Thus in one aspect the invention provides use of a therapeutic of the invention in the manufacture of a medicament for the treatment of a condition associated with IgE activation.

The invention also provides methods of treating a condition associated with IgE activation e.g. in an animal or human, comprising administering a therapeutically effective amount of a therapeutic of the invention.

The therapeutics of the invention may also be administered in combination with pharmaceuticals previously used in the treatment of a condition associated with IgE activation, such as inhaled corticosteroids, anti-IgE antibodies (e.g. omalizumab) and so on.

Identification of Modulator Mimetics by Structure-Function Studies

IGBPMA may be a source of functional mimetics sharing its IgE binding properties. The identification and use of such mimetics form further aspects of the present invention.

IGBPMA mimetics may not contain an active portion of the IGBPMA amino acid sequence, and indeed may not be peptides at all, but will retain the essential biological activity of IgE binding. Non polypeptide "small molecules" are often preferred for many in vivo pharmaceutical uses.

Examples of such mimetics include chemical compounds which are modeled to resemble the three dimensional structure of the IGBPMA polypeptide, or the IgE binding site thereof.

The IgE binding site on IGBPMA may be identified by methods well known to those skilled in the art, or using the methods discussed below.

The designing of mimetics to a known pharmaceutically active compound is a recognized approach to the development of pharmaceuticals based on a "lead" compound.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. Alanine scans of a peptide are commonly used to refine such peptide motifs. These parts or residues constituting the active region of the compound (in this case the IgE binding site) are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR.

The three dimensional structure may be determined by methods well known to those skilled in the art, as exemplified for example by "Three-Dimensional Solution Structure of alpha-Conotoxin MII, an alpha$_3$beta$_2$ Neuronal Nicotinic Acetylcholine Receptor-Targeted Ligand", Shon, et al. (1997) Biochemistry, vol. 36(50):15693-15700.

Computational analysis, similarity mapping (which models the charge and/or volume of a pharmacophore, rather than the bonding between atoms) and other techniques can be used in this modeling process.

In a variant of this approach, the three-dimensional structure of the ligand (i.e. IGBPMA polypeptide) and its binding partner (all or part of IgE) are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. Alternatively, where the mimetic is peptide based, further stability can be achieved by cyclising the peptide, increasing its rigidity. The mimetic or mimetics found by this approach can then be screened to see whether they have the target property, or to what extent they exhibit it. Further optimisation or modification can then be carried out to arrive at one or more final mimetics for in vivo or clinical testing.

Thus the present invention provides a method of providing (designing and\or producing) an IgE binder or modulator, which method comprises the steps of:
(i) providing an IGBPMA polypeptide as discussed above,
(ii) generating a 3 dimensional model of said polypeptide incorporating steric and charge information relating to said polypeptide (e.g. of the chemical groups of the polypeptide which interact with chemical groups of IgE); and
(iii) providing an IgE binding agent based on said steric and charge information (e.g. by identifying the relative spatial location of the chemical groups identified in (ii) of the polypeptide and designing a molecular mimetic which comprises some or all of the chemical groups in that spatial location).

The method may include synthesising and testing the molecular mimetic for its ability to bind an IgE molecule, using SPL and/or IgE affinity chromatography for example. A molecular mimetic which has binding affinity for an IgE molecule, which is similar to, or greater than, the binding affinity of the IGBPMA polypeptide may be selected as a molecular mimetic for use in the methods described above.

Identification of Alternative IgE Modulators

It is well known that pharmaceutical research leading to the identification of a new drug may involve the screening of very large numbers of candidate substances, both before and after a lead compound has been found. This is one factor which makes pharmaceutical research very expensive and time-consuming. Means for assisting in the screening process can have considerable commercial importance and utility.

The present invention provides, in a further aspect, a method of screening for further substances which bind or modulate IgE, the method generally comprising comparing under comparable reaction conditions binding of a detectable IGBPMA polypeptide to its cognate or respective binding site on IgE (generally provided by IgE or all or part of a constant region thereof) in the presence and absence of the test compound. IGMPMA polypeptides can be used to screen for substances in either a competitive or a displacement format.

Thus, in a further aspect of the present invention, IGBPMA polypeptides as provided herein are used in a method of screening for substances which affect, inhibit, modulate or mimic its activity or function with respect to IgE binding.

Example Methods Include
(i) Bringing together an IGBPMA polypeptide and its binding site on IgE and a putative IgE modulating agent; and
(ii) Observing, or measuring, the binding affinity of the IGBPMA polypeptide with the binding site on IgE, using SPL or IgE affinity chromatography, for example. When SPL is used to observe or measure the binding affinity, the polypeptide or the IgE molecule may be immobilised on a sensor chip.
(iii) Assessing whether the binding affinity of the IGBPMA polypeptide for the binding site on IgE is reduced in the presence of the agent, compared to the binding affinity of the polypeptide for the IgE molecule in the absence of the potential agent.

An agent which reduces the affinity of the IGBPMA polypeptide for the IgE molecule may be further tested for its ability to bind to an IgE molecule, using SPL or IgE affinity chromatography, for example. The binding affinity of an agent for an IgE molecule may be compared with the binding affinity of the polypeptide consisting of IGBPMA for IgE.

Another method of identifying agents which bind or modulate an IgE molecule may include the steps of:
(i) Bringing a putative agent into contact with an IgE molecule; and
(ii) Observing, or measuring, the binding affinity of the agent for the IgE molecule in the presence and absence of an IGBPMA polypeptide. The binding affinity of the agent for the IgE molecule may be observed, or measured, using SPL or IgE affinity chromatography, for example.
(iii) Assessing whether the binding affinity of the potential agent is similar to, or greater than, the binding affinity of the polypeptide, such as the polypeptide consisting of IGBPMA, for the IgE molecule.

In this and other aspects, the substances (putative IgE modulators) may be provided e.g. as the product of a combinatorial library such as are now well known in the art (see e.g. Newton (1997) Expert Opinion Therapeutic Patents, 7(10): 1183-1194).

Thus, in a displacement format, the invention provides a method for detecting the presence or amount of a putative IgE modulator in a sample, the method comprising the steps of:
(a) exposing the sample to a complex comprising detectable (e.g. labelled) IGBPMA or a variant polypeptide thereof immobilised to its binding site on IgE,
(b) detecting any displaced IGBPMA or variant polypeptide.

In competitive formats, all the components of the assay are brought together simultaneously and the reduction in binding of the IGBPMA or variant polypeptide in the presence of the putative IgE binder is determined. In one embodiment, a binding constant $K_d$ of the IGBPMA or variant polypeptide for the binding site on IgE is determined by a saturation binding method in which increasing quantities of radiolabeled peptide are added to the binding site on IgE, and the amount of labeled material bound at each concentration is determined. The appropriate binding equation describing the concentration of bound ligand as a function of the total ligand in equilibrium is fitted to the data to calculate the $B_{max}$ (the concentration of binding sites), and the $K_d$ (which is approximately the concentration of the ligand required for half saturation of binding sites).

Reversibility of binding is a characteristic of ligands which, under equilibrium conditions, freely associate with and dissociate from their respective binding sites. Reversibility of binding of a specific compound is demonstrated by the labelled compound's ability to be displaced by unlabelled compound, after equilibrium binding of the labelled compound has been achieved.

To determine the binding constant of a test compound for a IgE binding site for IGBPMA, the test compound is added, at increasing concentrations, to the binding site on IgE preparation in the presence of a standard concentration of IGBPMA or a variant thereof. The preparation is then rapidly filtered, washed and assayed for bound radiolabel. The binding constant $(K_i)$ of the test compound is determined from computer-fit competitive binding curves.

Essentially, methods of the present invention may be employed analogously or additionally to high throughput screens such as those well known in the art, and are based on binding partners—see e.g. WO 200016231(Navicyte); WO 200014540 (Tibotec); DE 19840545 (Jerini Biotools); WO 200012755 (Higher Council for Scientific Research); WO 200012705 (Pausch M H; Wess J); WO 200011216 (Bristol-Myers Squibb); U.S. Pat. No. 6,027,873 (Genencor Intl.); DE 19835071 (Carl Zeiss; F Hoffman-La Roche); WO 200003805 (CombiChem); WO 200002899 (Biocept); WO 200002045 (Euroscreen); U.S. Pat. No. 6,007,690 (Aclara Biosciences)

Further optimisation of any of the therapeutics of the present invention may comprise combining said therapeutic with (i) its binding site on IgE (generally provided by IgE or all or part of a constant region thereof); (ii) an IgE receptor with which said IgE or all or part of a constant region interacts pathologically in a condition associated with IgE activation. The degree to which said interaction is modulated, and in particular inhibited, is then assessed. Optionally the process is iterative in that the structure of the therapeutic is altered, or a close structural analog or variant is provided, and this is retested.

Agents identified as described above e.g. which bind IgE with an affinity similar to, or greater than, the binding affinity of IGBPMA may be selected and manufactured as an agent for use in a method of treating a condition associated with IgE activation as described in the preceding aspects.

Therapeutic Compositions and Modes of Administration

The therapeutics of the invention can be formulated into pharmaceutical compositions for use in the methods described herein.

These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, intramuscular, intraperitoneal routes—example formulations are discussed in WO95/27056.

Particularly of interest in the present application are inhalable formulations e.g. nasal insufflation, according to methods known in the art. Such therapeutics are particularly adapted for use in the treatment of conditions associated with IgE activation Polypeptide compositions suitable for inhalation are well known in the art—see e.g. U.S. Pat. No. 6,632,456; WO96/32096; WO91/16038 for example. Such pulmonary drug delivery compositions are designed to be delivered by inhalation of a drug dispersion by the patient so that the active drug within the dispersion can reach the lung. It has been found that certain drugs delivered to the lung are readily absorbed through the alveolar region directly into blood circulation.

Pulmonary drug delivery can itself be achieved by different approaches, including various types of liquid nebulizers, aerosol-based metered dose inhalers (MDI's), and dry powder dispersion devices. Dry powder dispersion devices are promising for delivering drugs that may be readily formulated as dry powders, particularly proteins and polypeptides. Preferred particle size will be in the range 0.5 to 10 µm.

A particularly promising approach for the pulmonary delivery of dry powder drugs utilizes a hand-held device with a hand pump for providing a source of pressurized gas. The pressurized gas is abruptly released through a powder dispersion device, such as a Venturi nozzle, and the dispersed powder made available for patient inhalation.

Thus the present invention provides a composition comprising a therapeutic of the present invention (particularly IGBPMA or variant polypeptide) in inhalable form, for example in the form of a dry powder of particle size 0.5 to 10 µm, more preferably less than 7 µm, and even more preferably less than 5 µm.

A pharmaceutical composition of the invention suitable for administration by inhalation may be included in a kit, together with an inhalation device which enables the pharmaceutical composition to be administered as a spray. Thus the present invention also provides a kit comprising a therapeutic of the present invention and delivery means for delivering the therapeutic by inhalation to a patient in need of the same. The delivery means may be any known in the art—e.g. a liquid nebulizer; an aerosol-based metered dose inhalers (MDI's), or a dry powder dispersion device. The delivery means will typically include a reservoir for holding the therapeutic, a source of pressurised gas (e.g. cylinder or pump) and a nozzle or other outlet for delivering it intranasaly.

Pharmaceutical compositions may also include other pharmaceuticals which are suitable for treating conditions associated with IgE activation, such as Omalizumab.

Administration of therapeutics of the present invention is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. Nucleic acid-based therapeutics of the invention may be used with conventioned gene therapy vectors, such as are well known in the art (see e.g. WO0159142).

Processes for Production

Processes for producing the therapeutics adapted for use in the treatment of conditions associated with IgE activation form a further aspect of the invention.

Additionally it is preferable that where such compositions comprise recombinantly produced polypeptides, they are substantially endotoxin free. This may be achieved, for example, using a Polymyxin agarose column.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

TABLES AND FIGURES

Table 1: shows estimations of relative binding activities (RBA) for three analytes: female SGED6, male SGED6, and female SalivaD7.

FIG. 1: The amino acid sequence (SEQ ID NO: 2) and DNA sequence (SEQ ID NO: 1) of IGBP-MA.

FIG. 2: Tick salivation induced by dopamine stimulation.

A. Salivation of males (triangle) and females (circles) following DA stimulation. X axis represents the mean of body weights (mg) of partially fed females and engorged males and females. Y axis represents the mean volume (µl) of saliva secreted by each tick. Error bars show the SEM (n=12-40).

B. Protein concentration in tick saliva. Columns show the means of total protein concentration (mg/l) in male and female saliva, respectively. Error bars represent the range of protein concentration. Two and eight batches of male and female saliva were used, respectively.

FIG. 3: Immunoglobulin binding activities in partially fed (day 6) female salivary gland extract. Lines A-E represent binding to IgG, IgE, Fc, F(ab')$_2$, and base line, respectively. White and black arrows indicate the start and stop points of analyte injection, respectively. After analyte injection ceased, flow cells were washed with TBS.

Figure 4:
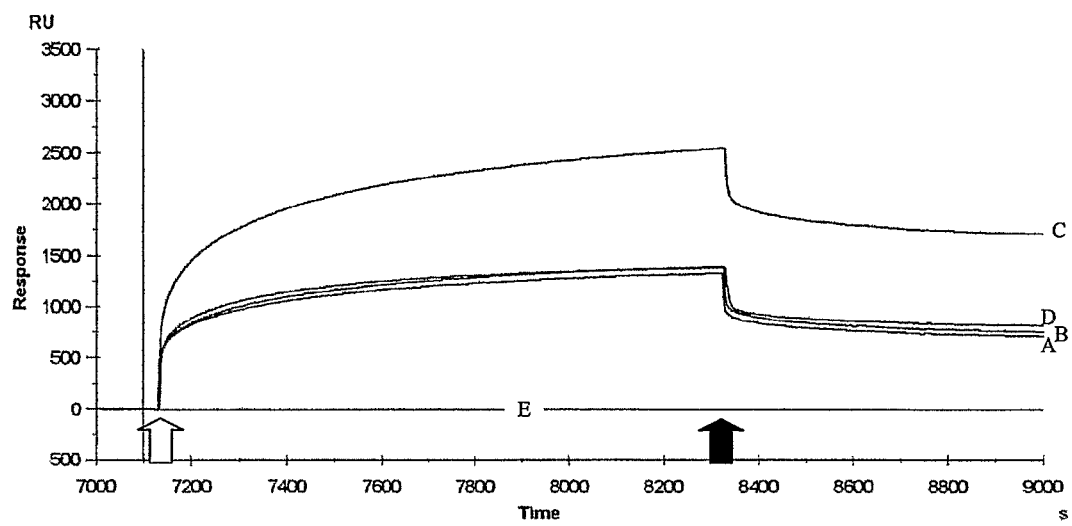

FIG. 4: Immunoglobulin binding activities in partially fed (day 6) male salivary gland extract. Lines A-E represent binding to IgG, IgE, Fc, F(ab')$_2$, and base line, respectively. White and black arrows indicate the start and stop points of analyte injection, respectively. After analyte injection ceased, flow cells were washed with TBS.

Figure 5:
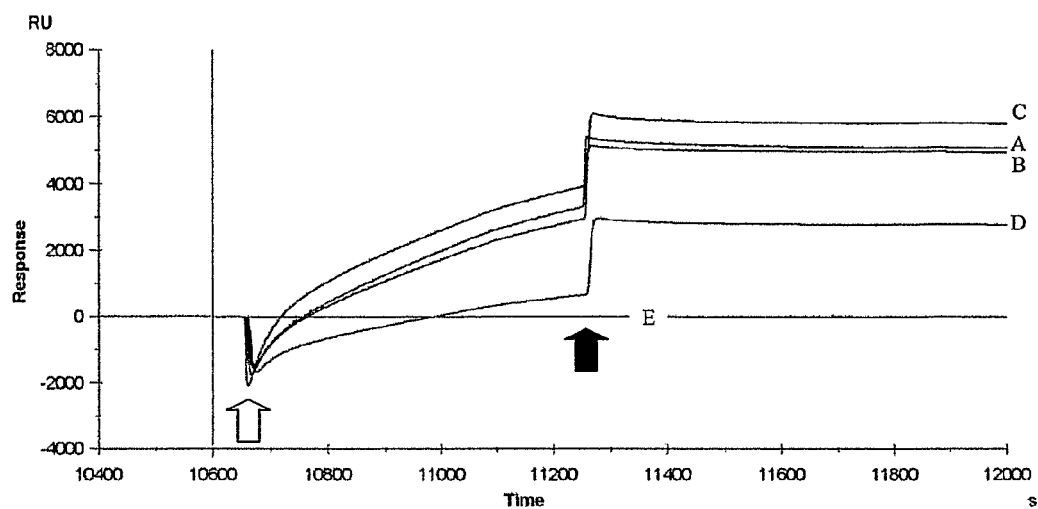

FIG. 5: Immunoglobulin binding activities in partially fed (day 7), dopamine-stimulated female saliva. Lines A-E represent binding to IgG, IgE, Fc, F(ab')$_2$, and base line, respectively. White and black arrows indicate the start and stop points of analyte injection, respectively. After analyte injection ceased, flow cells were washed by TBS.

Figure 6:
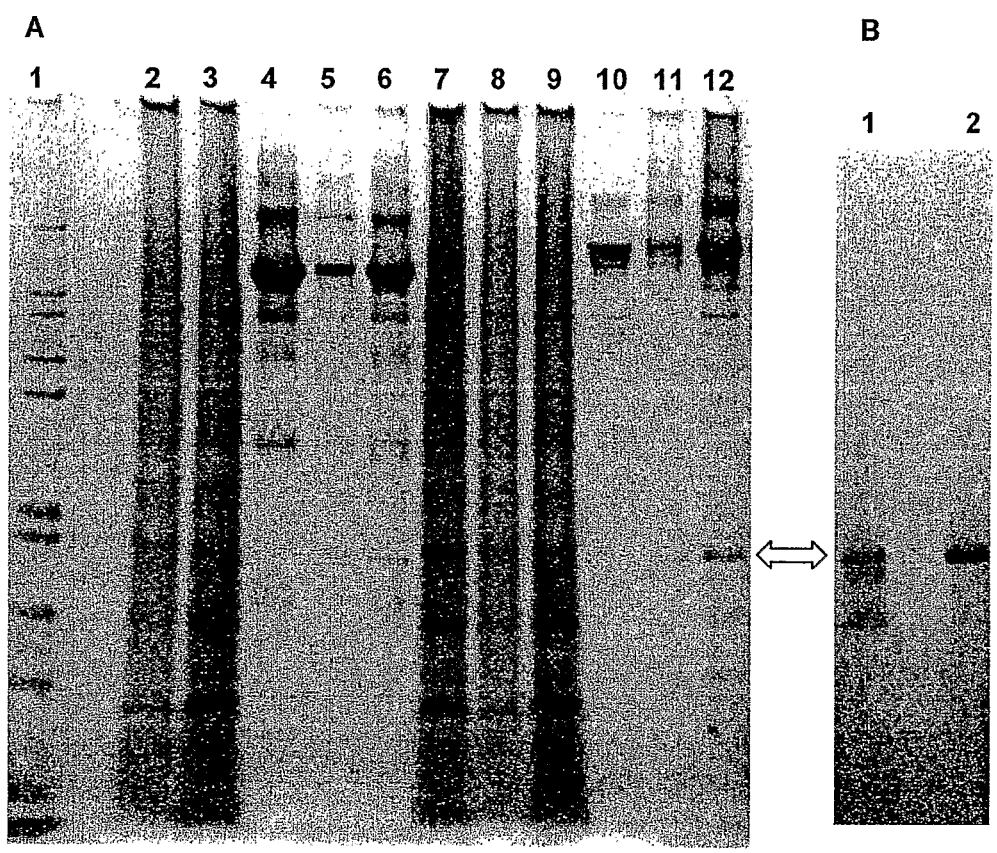

FIG. 6: IGBPMA in male SEGD6 binds to Guinea pig IgG and Rat IgE.

A. Protein gel (SDS-PAGE, non-reducing condition) shows total protein profile in male tick SGED6 and IGBPMA (indicated by arrow) was the major protein bound to both IgG and IgE.
   Lane 1: molecular weight (MW) marker (Mark-12, Invitrogen)
   Lanes 2 & 8: tick male SGED6 before loading
   Lane 3: tick male SGED6 running through Protein-L-IgG (G.pig) column (sample was concentrated)
   Lanes 7 & 9: tick male SGED6 running through Protein-L-IgE (rat) column (sample was concentrated)
   Lane 4: Guinea pig IgG
   Lanes 5 & 6: eluate fractions 1 and 2 of Protein-L-IgG (G.pig) column
   Lane 10: rat IgE
   Lanes 11 & 12: eluate fractions 1 and 2 of Protein-L-IgE (rat) column B. Western Blotting with anti-IGBP sera
   Lane 1: total protein of male SGED6. Bands from top are IGBPMA, -MB, and -MC
   Lane 2: eluate of Protein-L-IgE column FIG. 7: Screening of rIGBPMA expression.
A. Protein gel (SDS-PAGE, reducing condition)
B. Western Blotting with anti-IGBP sera
   Lanes 1-12: total E. coli cell lysate of individual clones induced for expressing rIGBPMA. The clone (No. F6) represented in Lane-3 was selected for all following experiments.
   Lane 13: male tick SGED6
   Lane 14: MW marker FIG. 8: Protein gel (SDS-PAGE, reducing condition) shows purified soluble rIGBPMA after refolding
   Lane 1: MW marker
   Lane 2: total protein in the insoluble fraction (6 M urea extract) of E. coli (Clone No. F6) cells after induction for rIGBPMA expression
   Lane 3: purified soluble rIGBPMA in TBS, arrow indicates rIGBPMA.

Figure 9:
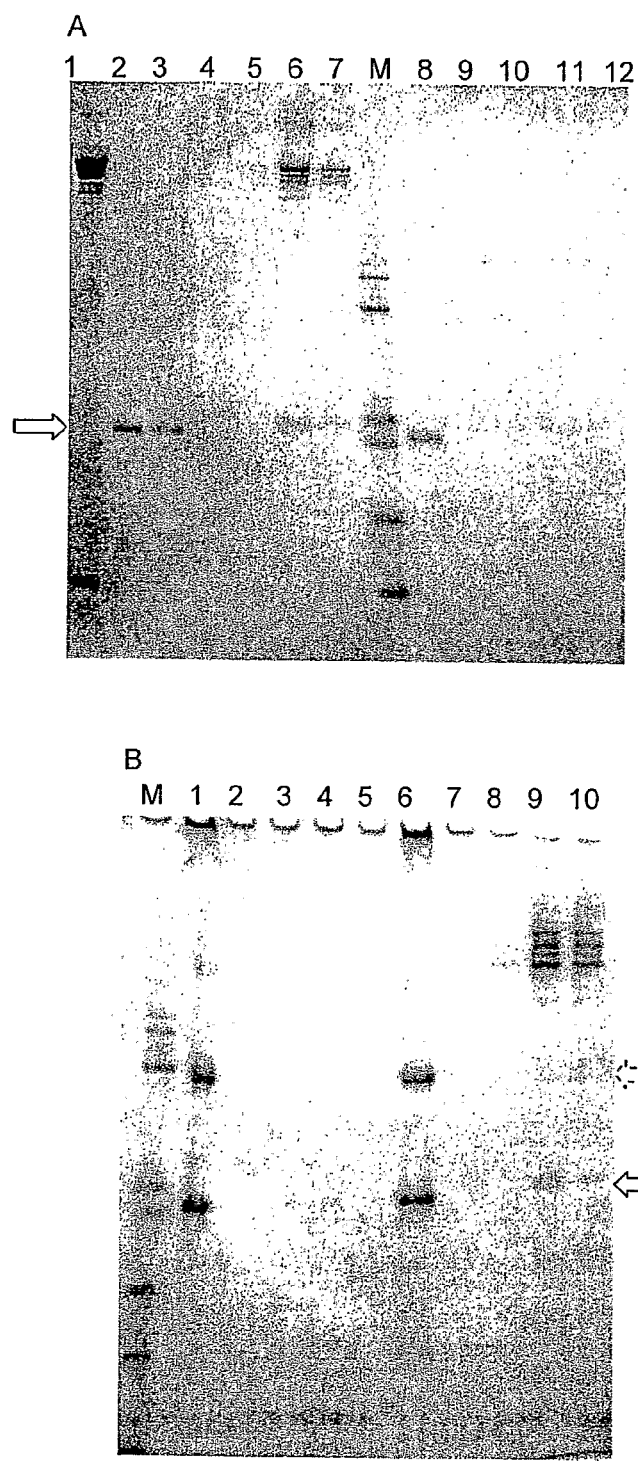

FIG. 9: Soluble rIGBPMA binds to human and rat IgE
Protein gels (SDS-PAGE, non-reducing condition) of samples from affinity columns (Protein-L-IgE) and control columns (Protein-L only)

A. Human-IgE
   Lanes 3-7: affinity (Protein-L-IgE) column
   Lanes 8-12: control (Protein-L) column
   Lane 1: human IgE
   Lane 2: purified rIGBPMA (arrow indication)
   Lane 3 & 8: rIGBPMA loaded
   Lanes 4 & 9: last washing fraction before elution
   Lanes 5 & 10: the 1$^{st}$ elution fraction
   Lanes 6 & 11: the 2$^{nd}$ elution fraction
   Lanes 7 & 12: the 3$^{rd}$ elution fraction
   M: MW marker B. Rat IgE
   Lanes 1-5: control (Protein-L) column
   Lanes 6-10: affinity (Protein-L-IgE) column
   Lanes 1 & 6: purified rIGBPMA (solid arrow) with BSA (dashed arrow) loaded onto the columns
   Lanes 2 & 7: the last washing fraction before elution
   Lanes 3 & 8: the 1$^{st}$ elution fraction
   Lanes 4 & 9: the 2$^{nd}$ elution fraction
   Lanes 5 & 10: the 3$^{rd}$ elution fraction FIG. 10: BIAcore 2000 detection of rIGBPMA binding to the Fc fragment
   Arrow-1 shows the start and arrow-2 shows the completion of rIGBPMA injection.
   Curve A: flow cell 4 with approx 4000 RU of Fc (human) fragment immobilized
   Curve B: flow cell 2 with approx 5000 RU of BSA immobilized
   Curve C: flow cell 3 with approx 5000 RU of F(ab)$_2$ (rabbit) fragment immobilized
   Curve: flow cell 1 as blank with no ligand immobilized FIG. 11: The effect of the rIGBPMA on allergic asthma in BALB/c mice.

Figure 12:
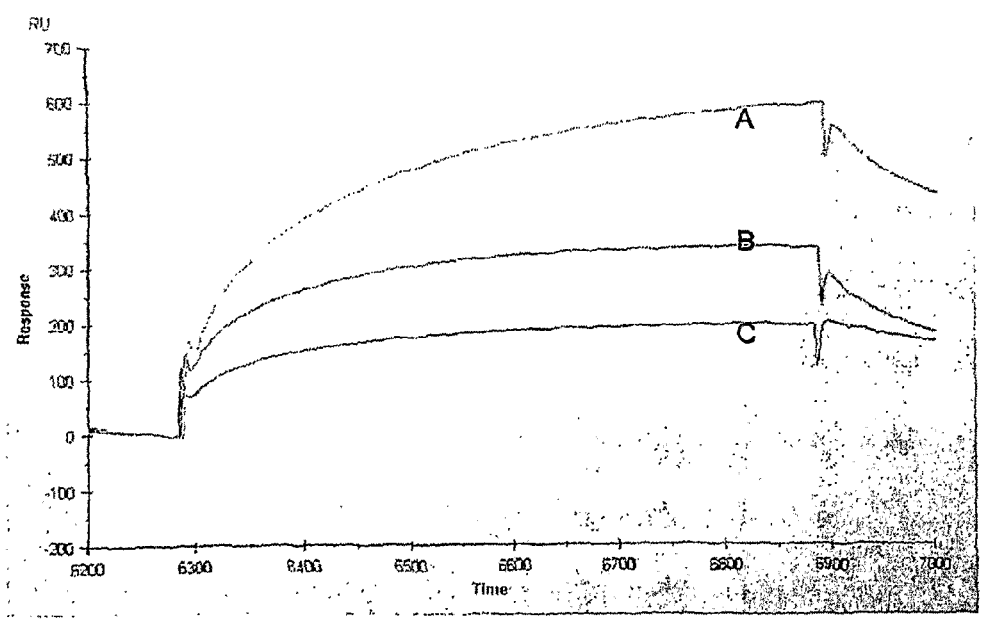

FIG. 12: Comparison of binding of rIGBPMA to IgE and IgG.
   Curve A: IgE
   Curve B: IgG
   Curve C: BSA

EXAMPLES

Materials and Methods

Ticks and Guinea Pigs

Our laboratory colony of R. appendiculatus is maintained by feeding all instars on the shaved backs of tick-naïve Dunkin Hartly guinea pigs (Jones et al., 1988). Female engorgement passes through the slow feeding phase then switches to the fast phase at about 6 days of feeding during which time females imbibe approximately 90% of the total bloodmeal (results not shown). Mating and subsequent male-female co-feeding occurs at about day 5 of female feeding (Wang, Henbest & Nuttall, 1999). For the Ig binding experiments, all of the ticks used were adults more than three months post-mounting. Twenty pairs of adults were fed on each of 3 guinea pigs for 6 days for salivary gland dissection, and 7 days for saliva collection.

Preparation of Tick Salivary Gland Extracts and Saliva

For example 1, partially fed adult ticks were removed from their hosts, rinsed three times in tap water, then dissected for salivary glands. Salivary gland extracts (SGE) were prepared from the paired glands of 50 ticks, in Tris-HCl buffered saline (TBS: 50 mM Tris, 150 mM NaCl, 20 mM CaCl$_2$, 20 mM MgCl$_2$, and 0.5% Triton-X100, pH 7.0) and stored as described previously (Wang & Nuttall, 1995b). The male and female SGEs were diluted in TBS to protein concentrations of 1 mg/ml and 2 mg/ml, respectively, as determined using a Bio-Rad protein assay kit (Bio-Rad).

To collect tick saliva, dopamine (DA) hydrochloride (Sigma) was dissolved in 1.2% NaCl to 5 mg/ml for stimulating tick salivation. Ticks were injected with DA (approximately 1 μl per 10 mg tick weight) through the camera-stomal fold (membrane covering the articulation between the mouthparts and the scutum) using a 30 g syringe needle attached to a Hamilton syringe. The method was modified from one previously described (Kaufman, 1978). Following injection, ticks were mounted dorsal side down on double-sided sticky tape and 5 μl or 10 μl capillary tubes placed over the mouthparts in such a way as to splay the palps apart, and to contain the chelicerae and hypostome within the capillary. To achieve a close (but not too tight) fit over the mouthparts, capillary tubes were drawn out slightly over a Bunsen burner, cut at the chosen point with a diamond pencil and fire-polished.

For the Ig binding experiments, the secreted saliva of 9 female ticks (fed for 7 days) was pooled into 1.5 ml microcentrifuge tubes containing 25 μl distilled water and held on ice; this initial aliquot of water was added to enable the rinsing of the capillary tubes to minimize loss of saliva. Saliva samples were stored at −70° C. until use, at which time the sample was measured for protein concentration and diluted to 0.1 mg/ml (protein concentration) by adding 5 μl of TBS (pH, and ionic strength of the saliva sample were not determined).

For example 2, adult male ticks that fed with females for 6 days, were removed from their hosts, rinsed three times in tap water, then dissected for salivary glands. Salivary gland extracts (SGE) were prepared from the paired glands of 30 ticks, in approximately 200 μl Tris-HCl buffered saline (TBS: 50 mM Tris, 150 mM NaCl, 20 mM $CaCl_2$, 20 mM $MgCl_2$, and 0.5% Triton-X100, pH 7.0) before being used for affinity chromatograph (Wang and Nuttall, 1995b).

Immobilization of Immunoglobulins onto a Biacore Chip

Purified immunoglobulins (guinea pig IgG, Sigma; rat recombinant IgE, Serotech; human IgG Fc, ICN; and rabbit IgG F(ab')$_2$, ICN) were dissolved to 1 mg/ml in phosphate buffered saline (PBS; 20 mM phosphate, 130 mM NaCl, pH 7.2). The built-in surface preparation wizard of BIAcore®2000 (BIAcore AB) was used to immobilize the immunoglobulins onto a sensor chip CM5 (BIAcore AB chip coated with carboxymethyl dextran) at a target level of 10,000 resonance units (RU) using standard amine coupling chemistry (as described in the BIAcore®2000 Instument Handbook and BIAapplication Handbook) at coupling pH 4.5 (10 mM acetate). The dextran layer of the CM5 chip is conducive for measuring protein interactions by providing a hydrophilic environment away from the flat biosensor surface. Onto each of the 4 flow cells in the sensor chip was immobilized either: (A) guinea pig IgG, (B) rat IgE, (C) human Fc fragment, or (D) rabbit F(ab')$_2$ fragment. The flow-cells were washed once with 100 μl of glycine buffered saline (GBS, 100 mM glycine, 150 mM NaCl, pH 2.6), then by 100 μl of TBS washing at a flow rate of 5 μl/min and stored at 4° C. overnight before use.

BIAcore2000 Detection of Immunoglobulin Binding Activities

All experiments were performed at room temperature (25° C.). All flow cells were injected with either 100 μl of tick SGEs (female or male) or 50 μl of female saliva at a flow rate of 5 μl/min. After each experiment, the flow cells were washed with 25 μl GBS (pH 2.6, see above) to remove bound tick material (analyte) and regenerate free immunoglobulins on the flow cell surface, followed by a wash of 200 μl TBS (pH 7.0, see above) before the next sample was tested.

Isolation of Ig-Binding Protein Using Protein-L Affinity Chromatograph

Protein-L linked agarose (Sigma) was used to make a 0.1 ml column. One hundred microliter of guinea pig IgG (Sigma, 1 mg/ml in TBS) or rat IgE (1 mg/ml, Serotech) were pre-incubated onto the column. The column was washed with TBS using more than 10 times the column volume. 200 μl of male tick SGE (D6) were loaded onto the column and recycled by a peristaltic pump for 1 hr. at 28° C. The column was washed with 1 ml of TBS 5 times, then eluted with 0.1 ml of GBS (100 mM Glycine, 150 mM NaCl, pH 2.6) three times. Proteins in the eluate were precipitated in trichloroacetic acid (TCA) at a final concentration of 20% (W/V), washed with cold acetone, redissolved in SDS-sample buffer (non-reducing, Invitrogen), boiled for 2 min., and examined by SDS-PAGE (10% Tricine pre-cast gel system, Invitrogen). The resulting gel was either stained with Coomassie brilliant blue or transferred onto nitrocellulose for Western blotting as described previously (Wang and Nuttall, 1995a).

RT-PCR Amplification, Cloning and Sequencing of IGBPMA

Total RNA of 30 day-6 fed male ticks was extracted into 0.1 ml of water using Qiagen RNA extraction kit. The full-length IGBPMA encoding sequence (SEQ ID NO: 1) was amplified by RT-PCR using primers (IGBPMA-1, nt 7-39 nt, AF001868; and IGBPMA-R1, reverse & complementary of nt 917-945, AF001868, 5'AGTGCGGCCGCTCCCT-TGACGTTACCGGACTTGAGGTCTA3' SEQ ID NO: 3). The RT-PCR product was cloned into pGEM-T vector (Promega) and fully sequenced from both directions by ABI technology. Obtained sequences were compared with the IGBPMA reference sequence in GenBank (AF001868) using BESTFIT in the GCG package.

Expression of Recombinant IGBPMA

Primers (IGBPMA-R1 and IGBPMA-F1, 5'AGTTCTA-GACATATGAAATACGAAGTGTACA-CAGGGCGCGGGGT3' SEQ ID NO: 4, nit 76-104, AT001868) were used to amplify the 5'-end truncated IGBPMA (mature form of IGBPMA as detected in tick SGE) encoding sequence from the fully sequenced new clone. The PCR product was cloned into the pET23 vector (NOvagen) in frame with a C-terminal 6-His-tag fusion, and used to transform BL21(DE3) E. coli host cells. Total cell lysates of 12 clones were examined for rIGBPMA expression after induction, by SDS-PAGE followed by Western blotting with anti-IGBP sera (Wang and Nuttall, 1995a). For large scale production, a single colony (Clone No F6) was cultured in 100 ml liquid LB (Amp') at 37° C. overnight, with a shaking speed of 200 rpm. The overnight culture was added to 1000 ml fresh pre-warmed liquid LB (Amp$^r$) and grown for 4 hr, to $OD_{600}$ 0.4-0.6 under the same conditions as for the overnight culture. Expression of recombinant IGBPMA (rIGBPMA) was induced by adding IPTG to a final concentration of 0.4 mM for 7 hr, at 37° C., 200 rpm.

Refolding, and Purification of rIGBPMA

The HisBind kits (Novagen) and the recommended method (Novagen) were used for purification of the riGBPMA. After extraction using BugBuster solution (Novagen), insoluble rIGBPMA from a 500 ml culture was extracted with 16 ml HisBind Binding Buffer containing 6 M of urea, and immobilised on a 1 ml Ni2+ charged HisBind column, and washed with 10×1 ml HisBind Washing Buffer containing 6 M urea. Refolding of rIGBPMA was performed in the HisBind column by washing the urea away with at least 10×1 ml the HisBind Washing Buffer at room temperature. The soluble fraction of rIGBPMA was eluted with 3×1 ml of HisBind Elution Buffer. Eluate was concentrated to 50 μl (Vivaspin 6, VivaScience) then diluted to 5 ml in TBS, and the process repeated 3 times to change the buffer conditions, then stored at −70° C.

Immunoglobulin-Binding Activities of rIGBPMA Determined Using Affinity Chromatograph rIGBPMA was centrifuged for 10 min at 13000 rpm after thawing, and the supernatant examined for Ig-binding activities. The IgG binding activity was determined using Human-IgG linked agarose (Sigma) as described previously (Wang and Nuttall, 1995a). Binding activity to Human-IgE (Serotech) and Rat-IgE (Serotech) was determined using a Protein-L affinity column as described above. Sepharose-6B (Sigma) and Protein-L agarose without IgE were used as control columns to the IgG and IgE systems, respectively. Bovine serum albumin (BSA) from a high concentration (10 mg/ml) stock was added to the purified soluble rIGBPMA before it was loaded onto the Protein-L-IgE column, to check the column specificity of rIGBPMA. Eluate from the affinity column was examined by SDS-PAGE as described above. To remove non-specific binding/aggregation, rIGBPMA supernatant was passed through a short Sepharose-6B (Sigma) column, then a Protein-L column, before being loaded onto the Protein-L-IgE affinity column.

Determination of Fc-Binding Activity of rIGBPMA by BIAcore2000

The method was as described above but a target level of 5,000 resonance units (RU) was used. Onto each of the 4 flow cells in the sensor chip was immobilize: Cell-1, blank; Cell-2, BSA (~5000 RU); Cell-3, rabbit F(ab')$_2$ fragment (~5000 RU); and Cell-4, human Fc fragment (~4000RU). The flow-cells were washed once with 30 μl of 20 mM HCl followed by at least 100 μl of TBS before use. 30 μl of rIGBPMA (1 mg/ml in TBS) was injected to flow over all flow-cells in the order of 1-2-3-4 at a flow rate of 10 μl/min.

Example 1

IgE Binding Activity in Tick Salivary Gland Extract and Saliva

Over a 30 min collection period, the volume of saliva secreted by females was proportional to body weight up to a threshold of approximately 75 mg above which it was maintained at about 10 μl per tick (FIG. 2A). Although the saliva volume from males was 10 to 100-fold less than that of females, the protein concentration of male saliva was significantly greater than that of females (FIG. 2B).

Three tick samples (female SGED6, male SGED6, and female SalivaD7) were used as comparative analytes to screen for binding against the four ligands immobilised in separate flow cells of a CM5 chip (FIGS. 3-5). The base line (E) denotes the zero reading before each tick sample was perfused through the ligand-immobilized flow cells. The rising portion of each curve denotes changes in macro-molecules on the chip surface (including the binding of analyte to the immobilized ligand). Following wash-out of non-specifically bound sample material with TBS (indicated by the black arrows in FIGS. 3-5), the final portion of each trace above the baseline was interpreted as specific binding of analyte to the ligand. Height of the line (final reading) is directly correlated to the amount of bound analyte. In the first experiment, female SGED6 showed binding to IgG, IgE and Fc but not to Fab (FIG. 3). The apparent absence of binding to Fab indicates that the observed binding to IgG, IgE and Fc is specific, and not due to aggregation or precipitation of analyte. After regenerating the biosensor chip, a second experiment conducted with male SGED6 revealed binding with all four ligands (FIG. 4). After further regeneration of the chip, a third experiment using female SalivaD7 showed binding with all four ligands (FIG. 5). The apparent difference in binding kinetics represented by the shape of the saliva curves (FIG. 5) compared to those of the SGE samples (FIGS. 3 and 4) may be due to the relatively low protein concentration of the saliva (0.1 mg/ml, see MATERIALS AND METHODS), and/or different buffer conditions of the saliva compared with SGE samples (pH and ionic strength of the analytes were unknown).

Table 1 shows estimations of relative binding activities (RBA) for the three analytes, namely female SGED6, male SGED6, and female SalivaD7. Response units (RU$_1$) of each ligand immobilized to the respective flow cell (determined using the BIAcore®2000 wizard), in proportion to respective molecular weights, were compared with IgG to determine relative molar amounts (RMA). Response units for each analyte were determined empirically (FIGS. 3-5). A quantitative comparison was then made of RBA of each analyte with each ligand. The comparative degree of binding to IgG normalized for protein content was: female salivaD7>male SGED6>female SGED6 (RBA/mg protein, Table 1). For all samples, binding to IgE was relatively stronger than binding to IgG (RBA$_{IgE}$/RBA$_{IgG}$≈1.2, Table 1).

Quantitative analysis confirmed that female SGED6 did not bind to F(ab')$_2$, while the binding of female SGED6 to the Fc component (RBAFC=1.1) was similar to the binding of IgG (RBA$_{IgG}$=1.0) (Table 1). In contrast to female SGED6, both male SGED6 and female salivaD7 bound to the F(ab')$_2$ component; the binding to Fc and F(ab')$_2$ was of similar potency in both cases (RBA$_{Fc}$/RBA$_{F(ab')2}$≈1.1, Table 1). For the male SGED6, IgG binding was marginally less than the total of Fc and F(ab')$_2$ binding (RBA$_{Fc}$=2.7 compared with RBA$_{Fc+F(ab')2}$=4.6, Table 1). The detected IgG binding activity of female SalivaD7 (RBA$_{Fc}$=19.4, Table 1) was close to the summed activities for Fc and F(ab')$_2$ binding (RBA$_{Fc+F(ab')2}$=15.7, Table 1).

Example 2

Immunoglobulin-Binding Activities of rIGBPMA Determined by Affinity Chromatography A 29 kD protein was isolated as the major band by the Protein-L-IgG (Guinea pig) affinity column as well as the Protein-L-IgE (Rat) affinity column from male SGED6 (FIG. 6A). The major band was recognised by antiserum raised against IGBPMA in Western Blotting (FIG. 6B). Other tick IgG-binding proteins (i.e. IGBPMB and IGBPMC) were not detected in the eluate of the IgE affinity column.

Sequencing of a new cline of IGBPMA from total RNA extract from day-6 fed male ticks of the same cohort used for IgE-binding protein isolation, only revealed one silent mutation (T-C) at nt-648 (SEQ ID NO: 1) of the IGBPMA reference sequence (GenBank, AF001868).

Figure 7:
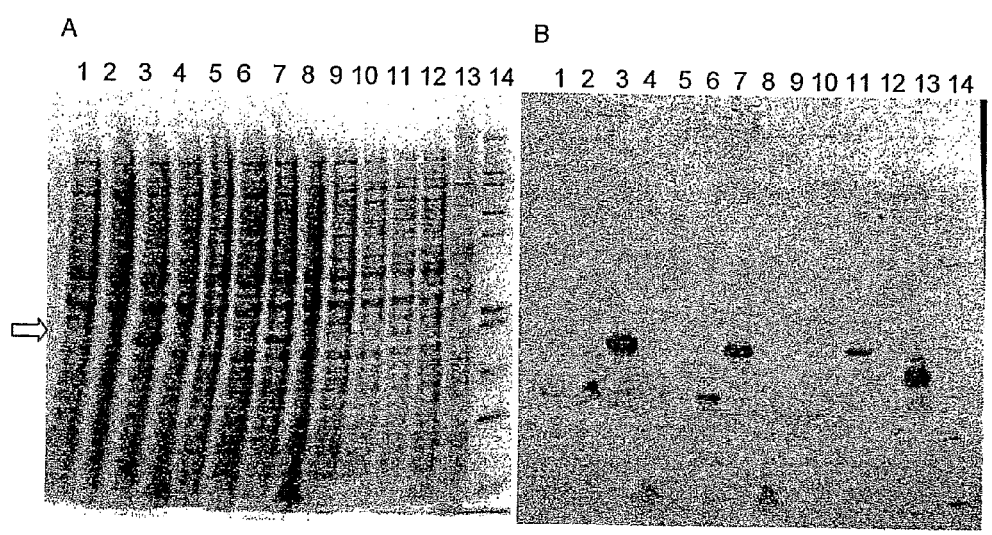
Figure 8:
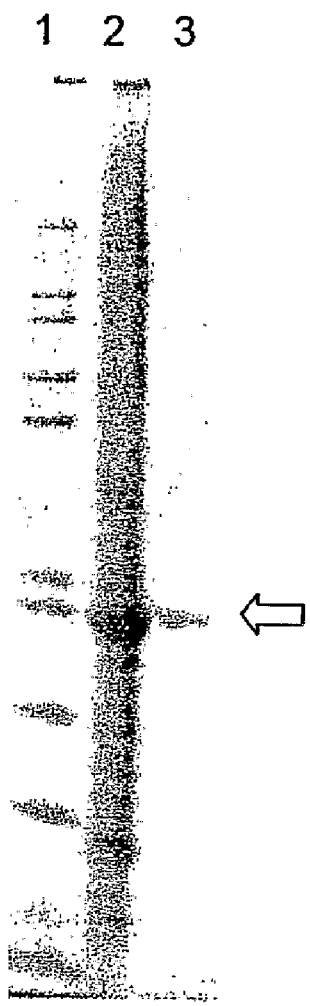

The N-terminal 26 amino acid truncated rIGBPMA was expressed abundantly in 3 BL21 (DE3) clones (FIG. 7). The rIGBPMA contains a C-terminal His-tag (6) that can be used for purification using a His-Bind column (Novagen). However, the rIGBPMA was insoluble in the cell lysate without denaturant urea. His-Bind Binding Buffer (Novagen) containing 6 M urea was used to solubilize the rIGBPMA and immobilize the denatured proteins onto the His-Bind column (Novagen) so that rIGBPMA could be isolated from the cell lysate by washing away un-bound E. coli proteins using His-Bind Washing Buffer (Novagen) contain 6 M urea. Fractions of the denatured rIGBPMA could be refolded into soluble forms when urea was removed from the His-Bind column by washing with the His-Bind Washing Buffer without urea. The soluble form(s) of rIGBPMA were eluted by the standard His-Bind Elution Buffer (Novagen) without denaturant and had high purity (FIG. 8). The yield was 5-10 mg rIGBPMA per liter of induced culture.

The soluble rIGBPMA purified from the His-Bind column contained binding activities to both IgG (human) (results not shown) and IgE (human, FIG. 9A; and rat, FIG. 9B), using human IgG-agarose (Sigma) and Protein-L-IgE (human, FIG. 9A; or rat, FIG. 9B) affinity columns, respectively. The refolded rIGBPMA also aggregated (presumably from non-natural forms) in the control columns (FIG. 9A, Protein-L agarose, Sigma) under some conditions. However, the bands of rIGBPMA from affinity columns were considerably stronger than those of control columns, indicating binding activities to the Ig molecules in the affinity columns. Adding BSA (as a control protein) to the affinity systems did not result in detection of BSA in the eluates (FIG. 9B), indicating that the rIGBPMA-IgG(E) binding activity is genuine. When rIGBPMA aggregates was removed before loading into the Protein-L-IgE (rat) affinity system, by running through a Sepharose-6B column then a Protein-L agarose column under the same conditions, the non-specific binding (FIG. 9A) in the control column (Protein-L column) was reduced to beyond detection while rIGBPMA binding activity to rat IgE remained detectable in the Protein-L-IgE column (FIG. 9B).

Figure 10:
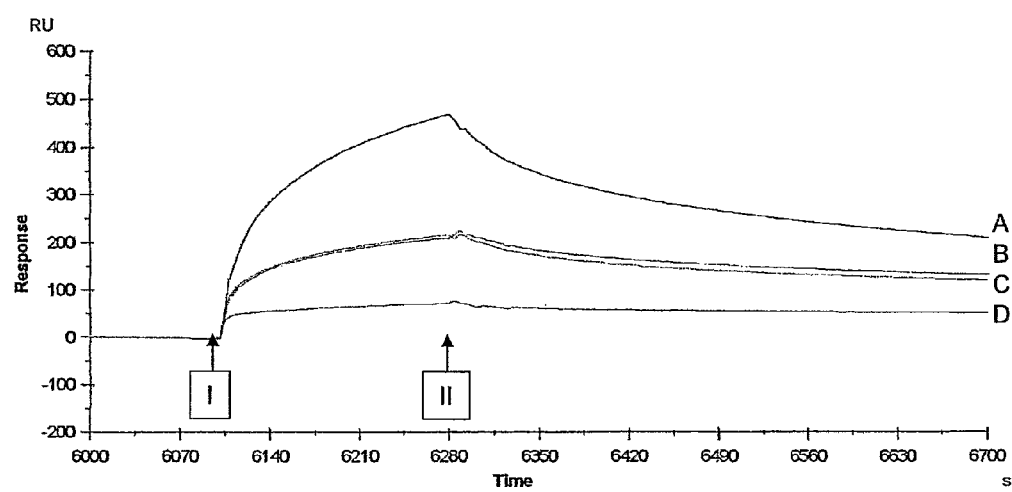
Figure 11:
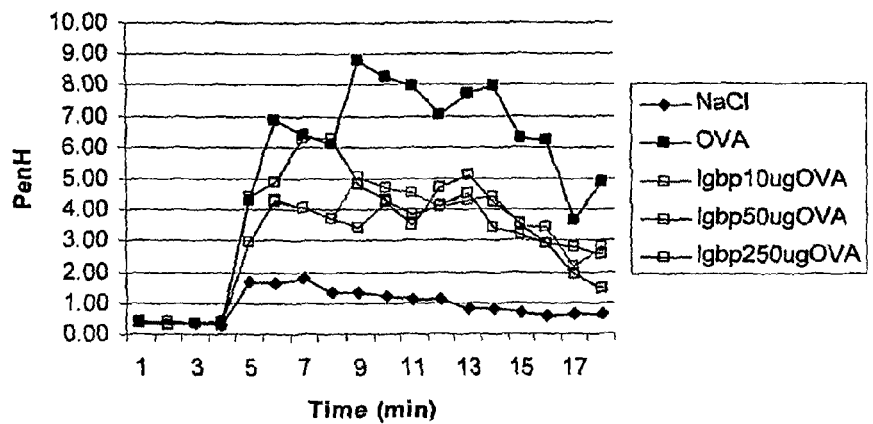

Using the BIAcore 2000, the rIGBPMA binding activities to immunoglobulins were shown to be due to binding affinity to the Fc fragment but not to the Fab fragment (FIG. 10). The F(ab)$_2$ fragment showed similar levels of non-specific binding with rIGBPMA (FIG. 10, curve C) as for BSA (FIG. 10, curve B). Binding to the Fc fragment (FIG. 10, curve A) was more than two times greater than such non-specific binding. Aggregation of rIGBPMA also occurred in the blank flow cell (FIG. 10, curve D). The Fc binding activity explains why rIGBPMA binds to both IgG and IgE molecules, and suggests that it may bind to a region that is conserved between the two Ig classes. If this is the case rIGBPMA is unlikely to bind to the receptor binding sites of these Ig molecules. Thus in addition to the free immunoglobulins in serum, rIGBPMA may also bind to the bound forms of IgG and IgE on cell surfaces. Mammalian IgG and IgE are presumed to be evolved from a common ancestor similar to the avian IgY, and are evolutionary divergent from the other mammalian immunoglobulins.

Example 3

Activity in BALB/c Mice

A recombinant protein (rIGBPMA, GenBank Accession number AF001868) derived from tick salivary glands was produced in *E. coli* as described above. By using endotoxin-free water in all steps during rIGBPMA purification, the endotoxin level can be reduced to approximately 50 EU/mg in purified rIGBPMA. When such rIGBPMA was tested by conventional methods (see for example Couillin et al. "Arthropod-Derived Histamine-Binding Protein Prevents Murine Allergic Asthma" *The Journal of Immunology*, 2004, 173: 3281-3286) for its effect on allergic asthma in BALB/c mice, it inhibited the allergic airway response (AHR) to methacholine in ovalbumin (OVA) sensitized (immunized) mice at low doses of 50 μg and 10 μg per mouse (see FIG. 11).

At high dose (250 μg per animal), however, rIGBPMA was less inhibitory to the early phase of AHR compared to the late phase. This may be due to the presence of bacterial lipopolysaccharide (LPS) (endotoxin) that induces AHR.

Example 4 rIGBPMA binds to IgE better than IgG

Purified human IgE (Serotech), Guinea pig IgG (Sigma), and BSA (Sigma) were immobilized onto a sensor chip CM5 (BIAcore AB chip coated with carboxymethyl dextran) by the Surface Preparation Wizard of BIAcore®2000 (BIAcore AB) at a target level of 5,000 resonance units (RU) using standard amine coupling chemistry (as described in the BIAcore®2000 Instrument Handbook and BIAapplication Handbook) at coupling pH 4.5 (10 mM acetate). Onto each of the 4 flow cells in the sensor chip was immobilized as: Cell-1, blank; Cell-2, BSA (4810 RU); Cell-3, IgG (5004 RU); and Cell-4, IgE (5780 RU). The flow-cells were washed once with 30 μl of 20 mM HCl followed by 100 μl of TBS before use. 50 μl of rIGBPMA (1 mg/ml in TBS, 50 mM Tris, 20 mM CaCl, 20 mM MgCl, 100 mM NaCl, pH 7.0) was injected to flow over all flow-cells at a flow rate of 5 μl/min.

As previously detected, rIGBPMA bound non-specifically to BSA (FIG. 12). However, above this background, rIGBPMA bound better to IgG and the best to IgE (FIG. 12). Although more IgE was immobilized on the chip than IgG (IgE, 5780 RU; IgG, 5004 RU), IgE had a binding signal (~430 RU) more than twice as high than that of IgG (~180 RU). This indicated that rIGBPMA bound to IgE better than IgG.

TABLE 1

Immunoglobulin immobilization and binding activities

| | | Flow-cell | | | |
|---|---|---|---|---|---|
| | | 1 | 2 | 3 | 4 |
| Ligand immobilized | | IgG | IgE | Fc | F(ab')$_2$ |
| Yield-immobilization (RU1) | | 10389 | 9149 | 7224 | 6693 |
| MW (kD)[#] | | 169 | 194 | 44 | 79 |
| Relative molar amount (RMA)* | | 1 | 0.8 | 2.7 | 1.4 |
| Yield-binding (RU2) | Female SGED6 (200 μg protein) | 263 | 283 | 748 | 13 |
| | Male SGED6 (100 μg protein) | 719 | 762 | 1718 | 823 |
| | Female salivaD7 (5 μg protein) | 5095 | 4957 | 5826 | 2773 |
| Relative binding activity (RBA)** | Female SGED6 | 1 | 1.3 | 1.1 | 0.0 |
| | Male SGED6 | 2.7 | 3.6 | 2.4 | 2.2 |
| | Female SalivaD7 | 19.4 | 23.6 | 8.2 | 7.5 |
| RBA/mg protein*** | Female SGED6 | 1 | 1.3 | 1.1 | 0.0 |
| | Male SGED6 | 5.5 | 7.3 | 4.9 | 4.5 |
| | Female SalivaD7 | 775 | 943 | 328 | 301 |

[#]The MW of each immunoglobulin (0.5 μg) was estimated from its mobility on SDS-PAGE under non-reducing conditions.
*Relative molar amount (RMA) of a ligand immobilized on the chip was normalized to that of the immobilized IgG. Thus, for each ligand (x), RMA$_x$ = (Yield$_x$/MW$_x$) ÷ (Yield$_{IgG}$/MW$_{IgG}$)
**Relative binding activity (RBA) for each tick sample (y) was normalized to the binding of fSGED6 to IgG after correcting for the RMA of the respective ligand (x). Thus, RBA$_y$ = (RU$_y$/RMA$_x$) ÷ (263/1).
***This panel further normalizes the data to the amount of protein (mg) in comparison to that in fSGED6. Thus, the RBAs for male SGED6 were doubled (half the protein of fSGED6) and the RBAs for female salivaD7 were multiplied by 40.

REFERENCES

Ackerman, S., Clare, F. B., McGill, T. W. & Sonenshine, D. E. (1981). Passage of host serum components, including antibody, across the digestive tract of *Dermacentor variabilis* (Say). *J Parasitol* 67, 737-740.

Allen, J. R., Khalil, H. M. & Graham, J. E. (1979). The location of tick salivary antigens, complement and immunoglobulin in the skin of guinea-pigs infested with *Dermacentor andersoni* larvae. *Immunology* 38, 467-472.

Beaudouin, E., Kanny, G., Guerin, B., Guerin, L., Plenat, F. & Moneret Vautrin, D. A. (1997). Unusual manifestations of hypersensitivity after a tick bite: report of two cases. *Ann Allergy Asthma Immunol* 79, 43-46.

Brossard, M. & Wikel, S. K. (1997). Immunology of interactions between ticks and hosts. *Medical and Veterinary Entomology* 11, 270-276.

Brown, S. J. & Askenase, P. W. (1985). Amblyomma americanum: requirement for host Fc receptors in antibody-mediated acquired immune resistance to ticks. *Exp Parasitol* 59, 248-256.

Brown, S. J., Worms, M. J. & Askenase, P. W. (1983). *Rhipicephalus appendiculatus*: larval feeding sites in guinea pigs actively sensitized and receiving immune serum. *Exp Parasitol* 55, 111-120.

Chinzei, Y. & Minoura, H. (1987). Host immunoglobulin G titre and antibody activity in haemolymph of the tick, Ornithodoros moubata. *Med Vet Entomol* 1, 409-416.

Christe, M., Rutti, B. & Brossard, M. (1999). Influence of the genetic background and parasite load of mice on the immune response developed against nymphs of *Ixodes ricinus*. *Parasitol Res* 85, 557-561.

Daeron, M. (1997). Fc receptor biology. *Annu Rev Immunol* 15, 203-234.

Enriquez, F. J., Boggavarapu, J. & Bradley Dunlop, D. (1992). Presence of non-Fab IgE binding molecules in the intestinal nematode parasite of mice *Heligmosomoides polygyrus*. *Int Arch Allergy Immunol* 99, 123-126.

Fivaz, B. H. (1990). Immunological responses of the rabbit host to infestation by the brown ear-tick *Rhipicephalus appendiculatus* (Acarina:Ixodidae). *Exp Appl Acarol* 9, 219-238.

Jones, L. D., Davies, C. R., Steele, G. M. & Nuttall, P. A. (1988). The rearing and maintenance of ixodid and argasid ticks in the laboratory. *Animal Technology* 39, 99-106.

Kaufman, W. R. (1978). Actions of some transmitters and their antagonists on salivary secretion in a tick. *Am J Physiol* 235, R76-81.

Kinet, J. P. (1999). The high-affinity IgE receptor (Fc epsilon R1): from physiology to pathology. *Annu Rev Immunol* 17, 931-972.

Matsuda, H., Watanabe, N., Kiso, Y., Hirota, S., Ushio, H., Kannan, Y., Azuma, M., Koyama, H. & Kitamura, Y. (1990). Necessity of IgE antibodies and mast cells for manifestation of resistance against larval *Haemaphysalis longicornis* ticks in mice. *J Immunol* 144, 259-262.

Mitchell, E. B., Brown, S. J. & Askenase, P. W. (1982). IgG1 antibody-dependent mediator release after passive systemic sensitization of basophils arriving at cutaneous basophil hypersensitivity reactions. *J Immunol* 129, 1663-1669.

Noben, N. N., Wilson, M. E. & Lynch, R. G. (1994). Modulation of the low-affinity IgE Fc receptor (Fc epsilon RII/CD23) by *Leishmania chagasi*. *Int Immunol* 6, 935-945.

Nuttall, P. A. (1998). Displaced tick-parasite interactions at the host interface. *Parasitology* 116, S65-S72.

Szabo, M. P. & Bechara, G. H. (1999). Sequential histopathology at the *Rhipicephalus sanguineus* tick feeding site on dogs and guinea pigs. *Exp Appl Acarol* 23, 915-928.

Tracey Patte, P. D., Kemp, D. H. & Johnston, L. A. (1987). *Boophilus microplus*: passage of bovine immunoglobulins and albumin across the gut of cattle ticks feeding on normal or vaccinated cattle. *Res Vet Sci* 43, 287-290.

Ushio, H., Watanabe, N., Kiso, Y., Higuchi, S. & Matsuda, H. (1993). Protective immunity and mast cell and eosinophil responses in mice infested with larval *Haemaphysalis longicornis* ticks. *Parasite Immunol* 15, 209-214.

Vincendeau, P. & Daeron, M. (1989). *Trypanosoma musculi* co-express several receptors binding rodent IgM, IgE, and IgG subclasses. *J Immunol* 142, 1702-1709.

Wang, H., Henbest, P. J. & Nuttall, P. A. (1999). Successful interrupted feeding of adult *Rhipicephalus appendiculatus* (Ixodidae) is accompanied by re-programming of salivary gland protein expression. *Parasitology* 119, 143-149.

Wang, H. & Nuttall, P. A. (1994). Excretion of host immunoglobulin in tick saliva and detection of IgG-binding proteins in tick haemolymph and salivary glands [published erratum appears in Parasitology 1995 April; 110(Pt 3):363]. *Parasitology* 109, 525-530.

Wang, H. & Nuttall, P. A. (1995a). Immunoglobulin G binding proteins in male *Rhipicephalus appendiculatus* ticks. *Parasite Immunol* 17, 517-524.

Wang, H. & Nuttall, P. A. (1995b). Immunoglobulin-G binding proteins in the ixodid ticks, *Rhipicephalus appendiculatus, Amblyomma variegatum* and *Ixodes hexagonus*. *Parasitology* 111, 161-165.

Wang, H. & Nuttall, P. A. (1999). Immunoglobulin-binding proteins in ticks: new target for vaccine development against a blood-feeding parasite. *Cellular and Molecular Life Sciences* 56, 286-295.

Wang, H., Paesen, G. C., Nuttall, P. A. & Barbour, A. G. (1998). Male ticks help their mates to feed. *Nature* 391, 753-754.

Worms, M. J., Askenase, P. W. & Brown, S. J. (1988). Requirement for host Fc receptors and IgG antibodies in host immune responses against *Rhipicephalus appendiculatus*. *Vet Parasitol* 28, 153-161.

---

The invention claimed is:

1. A method of treating a Type 1 hypersensitivity reaction administering to a subject in need thereof an agent which is a polypeptide, the polypeptide comprising:
   (i) the IGBPMA amino acid sequence SEQ ID NO:2, or
   (ii) a truncated form of the IGBPMA amino acid sequence SEQ ID NO:2 which lacks the N-terminal 26 amino acids thereof,
wherein in each case the polypeptide is capable of binding an IgE molecule.

2. A method of treating asthma, eczema, allergic rhinitis, rhinorrhea, conjunctivitis, gastroenteritis, or urticaria, comprising administering to a subject in need thereof an agent which is a polypeptide, the polypeptide comprising:
   (i) the IGBPMA amino acid sequence SEQ ID NO:2, or
   (ii) a truncated form of the IGBPMA amino acid sequence SEQ ID NO:2 which lacks the N-terminal 26 amino acids thereof,
wherein in each case the polypeptide is capable of binding an IgE molecule.

* * * * *